United States Patent
Robert et al.

(10) Patent No.: US 9,421,291 B2
(45) Date of Patent: Aug. 23, 2016

(54) HAND DRYER WITH SANITIZING IONIZATION ASSEMBLY

(71) Applicants: Michael E. Robert, Farmington Hills, MI (US); Charles H. Waddell, Roanoke, VA (US); Joseph A. Christiansen, Savannah, GA (US)

(72) Inventors: Michael E. Robert, Farmington Hills, MI (US); Charles H. Waddell, Roanoke, VA (US); Joseph A. Christiansen, Savannah, GA (US)

(73) Assignee: Fifth Third Bank, Cincinnati, OH (US)

( * ) Notice: Subject to any disclaimer, the term of this patent is extended or adjusted under 35 U.S.C. 154(b) by 0 days.

(21) Appl. No.: 13/850,815

(22) Filed: Mar. 26, 2013

(65) Prior Publication Data

US 2013/0232807 A1   Sep. 12, 2013

Related U.S. Application Data

(63) Continuation of application No. PCT/US2012/067506, filed on Dec. 2, 2012, which is a continuation of application No. 13/751,491, filed on Jan. 28, 2013, application No. 13/850,815, which is a continuation of application No. 13/188,764, filed on Jul. 22, 2011, now Pat. No. 8,861,167.

(60) Provisional application No. 61/566,413, filed on Dec. 2, 2011, provisional application No. 61/485,178, filed on May 12, 2011, provisional application No. 61/660,301, filed on Jun. 15, 2012.

(51) Int. Cl.
| | | |
|---|---|---|
| A61L 2/14 | (2006.01) |
| B03C 3/38 | (2006.01) |
| B03C 3/41 | (2006.01) |
| B03C 3/70 | (2006.01) |
| B03C 3/86 | (2006.01) |
| F26B 21/00 | (2006.01) |

(52) U.S. Cl.
CPC .............. *A61L 2/14* (2013.01); *B03C 3/383* (2013.01); *B03C 3/41* (2013.01); *B03C 3/70* (2013.01); *B03C 3/86* (2013.01); *F26B 21/003* (2013.01); *B03C 2201/08* (2013.01); *B03C 2201/10* (2013.01)

(58) Field of Classification Search
CPC ....... A61L 2/14; F26B 21/003; B03C 3/383; B03C 3/41; B03C 3/70; B03C 3/86
See application file for complete search history.

(56) References Cited

U.S. PATENT DOCUMENTS 2,577,809 A   12/1951   Reeves et al.
3,584,766 A   6/1971   Hart et al.
(Continued)

FOREIGN PATENT DOCUMENTS

EP   2327327 A1   6/2011
GB   2358350   *   7/2001   ............. A47K 10/48
(Continued)

OTHER PUBLICATIONS

International Search Report mailed Mar. 28, 2013 (PCT/US2013/023528).

*Primary Examiner* — Zeev V Kitov
(74) *Attorney, Agent, or Firm* — Dickinson Wright PLLC

(57) ABSTRACT

A hand dryer assembly including a blower assembly for generating a moving air stream. The moving air stream passes through an air channel to an air outlet where it exits the hand dryer assembly. An ionization assembly is disposed along the air channel and emits charged ions directly into the moving air stream, sanitizing the hands of the user, the moving air steam, and the ambient air that is entrained into the moving air stream.

26 Claims, 26 Drawing Sheets

(56) References Cited

U.S. PATENT DOCUMENTS

| | | | |
|---|---|---|---|
| 3,704,572 A * | 12/1972 | Gourdine et al. | 96/58 |
| 3,873,835 A | 3/1975 | Ignatjev | |
| 3,948,601 A | 4/1976 | Fraser et al. | |
| 4,596,921 A | 6/1986 | Hersh et al. | |
| 4,625,119 A | 11/1986 | Murdock, III | |
| 4,729,057 A * | 3/1988 | Halleck | 361/213 |
| 4,794,225 A * | 12/1988 | Maese | 392/385 |
| 4,931,261 A | 6/1990 | Jacob | |
| 5,200,146 A | 4/1993 | Goodman | |
| 5,459,944 A | 10/1995 | Tatsutani et al. | |
| 5,560,120 A | 10/1996 | Swanson et al. | |
| 5,828,063 A * | 10/1998 | Koster et al. | 250/288 |
| 5,874,166 A * | 2/1999 | Chu et al. | 428/368 |
| 6,077,334 A * | 6/2000 | Joannou | 96/66 |
| 6,130,815 A * | 10/2000 | Pitel et al. | 361/212 |
| 6,640,049 B1 | 10/2003 | Lee et al. | |
| 6,645,435 B2 | 11/2003 | Dawson et al. | |
| 6,705,428 B2 | 3/2004 | Kudernatsch | |
| 6,717,414 B1 * | 4/2004 | Rodrigo et al. | 324/464 |
| 6,730,238 B2 | 5/2004 | Li et al. | |
| 6,785,114 B2 * | 8/2004 | Gorczyca et al. | 361/231 |
| 6,874,697 B2 | 4/2005 | Callueng | |
| 7,878,371 B2 | 2/2011 | Sassoon | |
| 7,946,055 B2 | 5/2011 | Churchill et al. | |
| 7,989,779 B1 | 8/2011 | Ray et al. | |
| 8,037,691 B2 | 10/2011 | Commaret et al. | |
| 8,064,756 B2 | 11/2011 | Liu | |
| D661,023 S | 5/2012 | Liu et al. | |
| 2002/0005116 A1 * | 1/2002 | Hagglund | B03C 3/12 95/79 |
| 2004/0026530 A1 | 2/2004 | Callueng | |
| 2006/0244386 A1 | 11/2006 | Hooke et al. | |
| 2006/0272673 A1 | 12/2006 | Kurunczi | |
| 2008/0253754 A1 * | 10/2008 | Rubin | 392/381 |
| 2009/0119942 A1 | 5/2009 | Aisenberg et al. | |
| 2010/0247389 A1 | 9/2010 | Abate | |
| 2010/0254853 A1 | 10/2010 | Lee et al. | |
| 2011/0116967 A1 | 5/2011 | Roy et al. | |
| 2011/0277342 A1 | 11/2011 | Ishii et al. | |
| 2012/0200982 A1 * | 8/2012 | Partridge | 361/213 |
| 2012/0285033 A1 | 11/2012 | Hsu | |
| 2013/0025045 A1 | 1/2013 | Gagnon et al. | |
| 2013/0031799 A1 * | 2/2013 | Gagnon et al. | 34/526 |
| 2013/0232807 A1 | 9/2013 | Robert et al. | |

FOREIGN PATENT DOCUMENTS

| | | | | |
|---|---|---|---|---|
| GB | 2380676 | * | 4/2003 | A61L 9/22 |
| JP | 2001019606 | * | 2/2011 | A47K 10/48 |
| WO | 2007067924 A2 | | 6/2007 | |
| WO | 2012135830 A1 | | 10/2012 | |

* cited by examiner

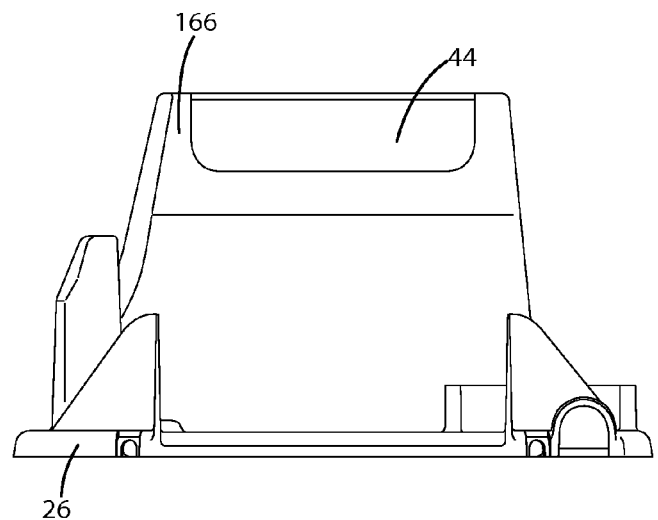
Fig. 28
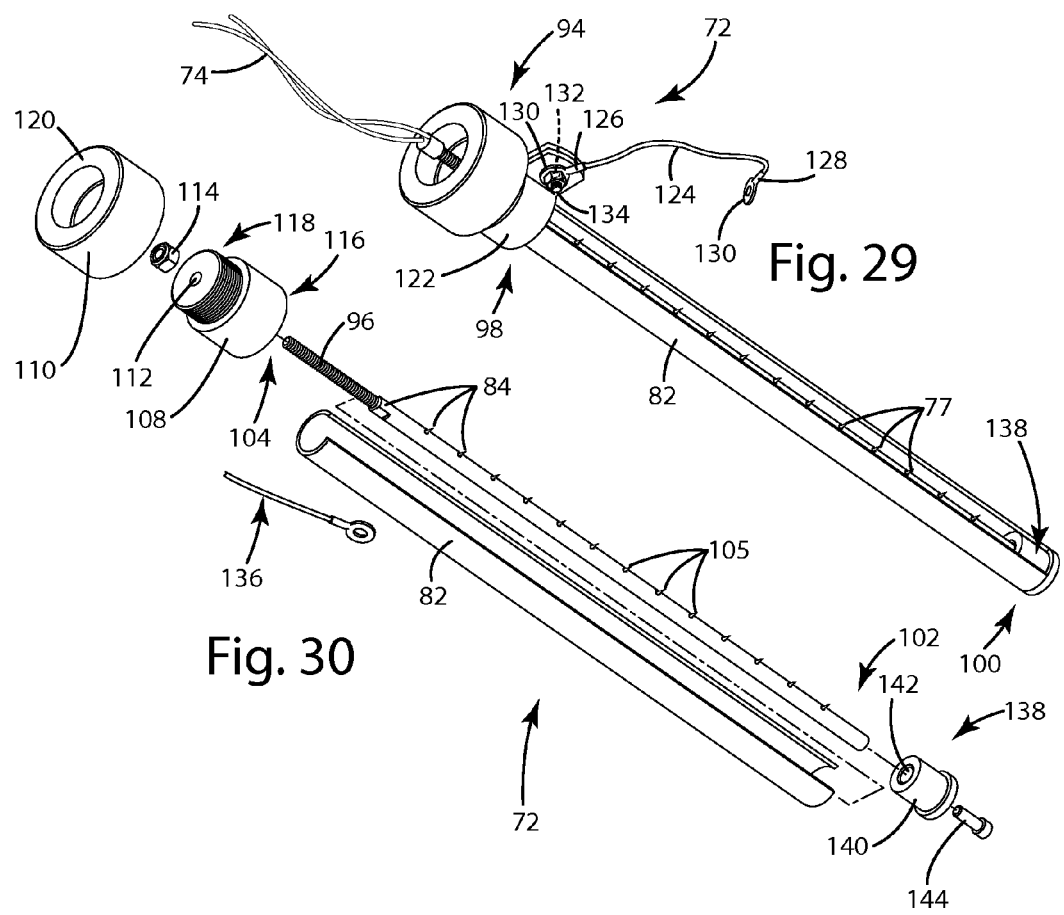
Fig. 29
Fig. 30

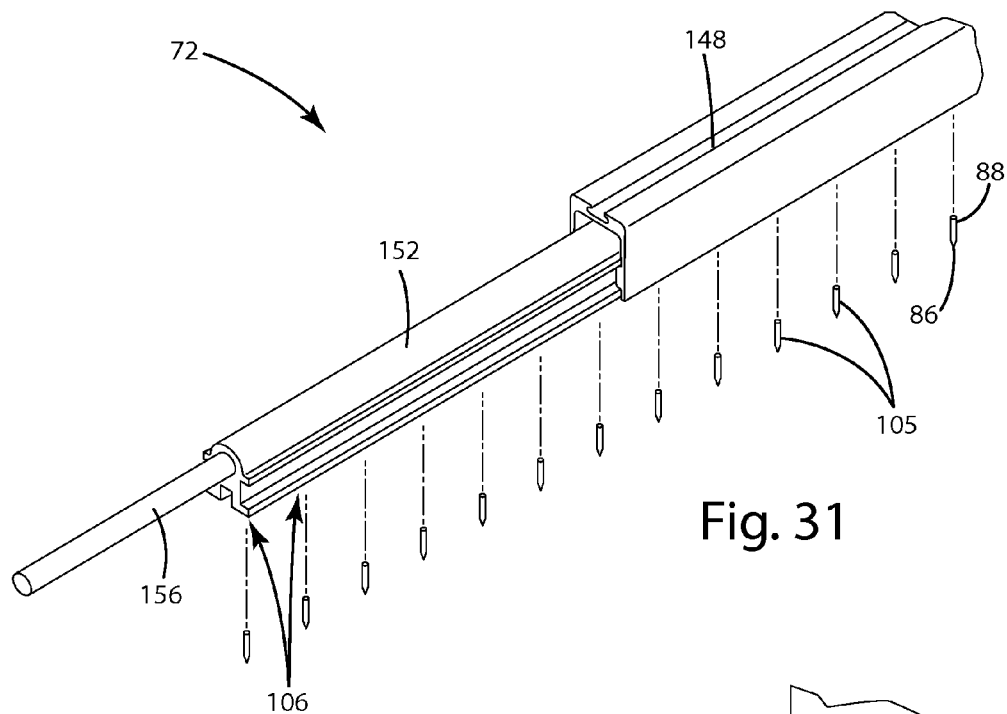
Fig. 31
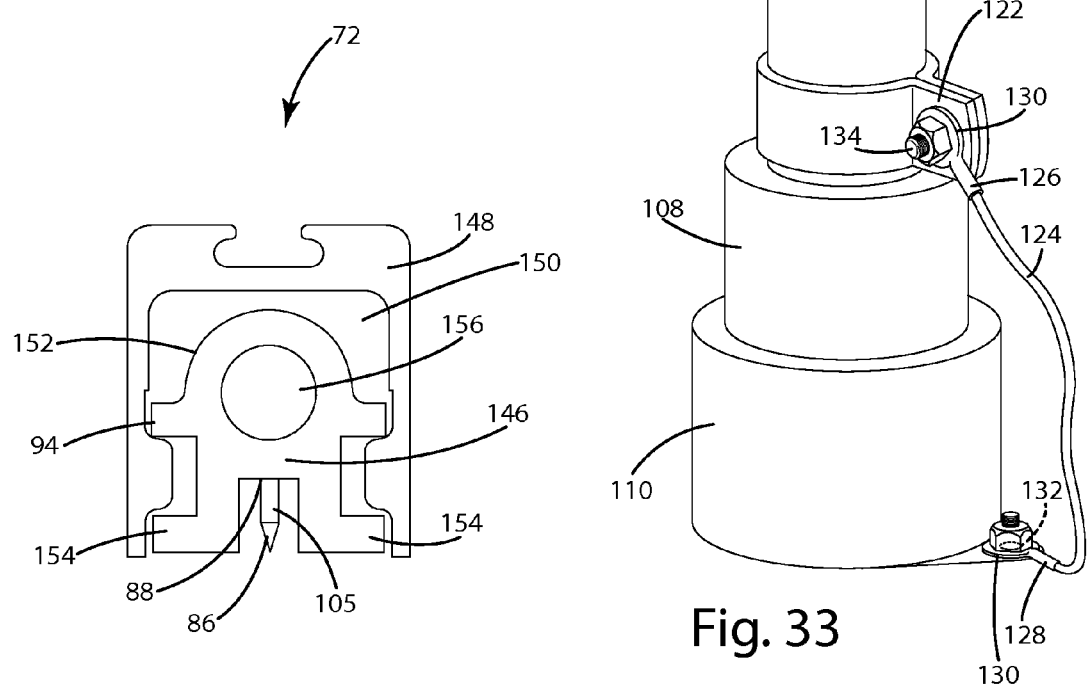
Fig. 32
Fig. 33

HAND DRYER WITH SANITIZING IONIZATION ASSEMBLY

CROSS REFERENCE TO RELATED APPLICATION

This application is a continuation-in-part of PCT Patent Application Serial Number PCT/US12/67506 filed Dec. 2, 2012, entitled "Dryer And Splash Guard" which claims priority to U.S. Provisional Patent Application Ser. No. 61/566,413 filed Dec. 2, 2011, entitled "Splash Guard For Hand Dryers And Low Surface Mount ADA Compliant Hand Dryer," claims priority to U.S. patent application Ser. No. 13/751,491 filed Jan. 28, 2013, entitled "Backplate" and U.S. Provisional Patent Application Ser. No. 61/660,301 filed Jun. 15, 2012, entitled "Ion Generation Device," and claims priority to U.S. patent application Ser. No. 13/188,764 filed Jul. 22, 2011, entitled "Bipolar Ionization Device" and U.S. Provisional Patent Application Ser. No. 61/485,178 filed May 12, 2011, entitled "Permanent Bi-polar Ionization Tube," with the entirety of said applications being considered part of the disclosure of this application and hereby incorporated by reference.

BACKGROUND OF THE INVENTION

1. Field of the Invention

The present invention is generally directed to a hand dryer assembly for drying the hands of a user, and more particularly to a hand dryer assembly that includes an ionization assembly emitting charged ions into the moving air stream produced by the hand dryer assembly to sanitize the moving air stream, the surrounding air pulled into the moving air stream, the hands of the user, and surfaces of the hand dryer assembly and any surfaces adjacent thereto.

2. Description of the Prior Art

Wall or surface mounted hand dryer assemblies have been used for many years in washrooms, locker rooms, and the like for drying a user's hands after washing. Originally, most of these hand dryer assemblies produced a low velocity moving air stream, causing the drying process of the hands to be fairly slow. To speed up the drying process, many manufactures created high-speed or high velocity hand dryer assemblies. Both low and high velocity hand dryer assemblies are advantageous over traditional paper towel dispensers in several respects. Namely, hand dryer assemblies eliminate paper towel usage and its associated cost to the facility and the environment. Hand dryer assemblies promote low maintenance facilities as less trash is generated when paper towel use is eliminated.

Typical hand dryer assemblies that are known in the art generally include a backplate configured to be mounted against a support structure such as a wall. An outer shell is attached to the backplate with the outer shell including an air inlet for receiving ambient air disposed outside of the outer shell and a blower assembly is located within the cavity of the outer shell. The blower assembly generates a moving air stream which exits from a nozzle extending through the outer shell. Operation of the blower assembly is accomplished by either a push button disposed on the outer shell or a motion sensor detecting the presence of the hands of the user adjacent the nozzle.

Such hand dryer assemblies also present some drawbacks. Washrooms, by their nature, may contain unusually high amounts of bacteria, viruses, and other pathogens. These microorganisms and the like may contaminate the surfaces of the washroom as well as the ambient air even when the washroom is diligently cleaned. Hand dryer assemblies must operate within this hostile environment. Concern is that the moving air stream produced by the hand dryer assembly may contain high concentrations of airborne microorganisms since the hand dryer assembly draws in ambient air from the washroom. To address this problem, some manufactures have added various filters, including HEPA filters, to remove many of these microorganisms from the moving air stream.

The addition of the filter to the hand dryer assembly presents several drawbacks and may have a limited effect. First, filters must be changed periodically and therefore add to the maintenance of the hand dryer assembly. Second, as filters traditionally were not common, many facilities do not have procedures in place for regularly changing filters in hand dryer assemblies. All of the above add to the operating costs of the hand dryer assembly, well beyond the purchase price of replacement filters. Third, as many wall mounted hand dryer assemblies are placed in high use or high crime areas, they are manufactured to be vandal resistant, which makes changing the filter more difficult. Fourth, while traditional hand dryer assemblies that do not employ filters are fairly maintenance free, if a filter is not regularly replaced, the performance of the hand dryer assembly will degrade significantly over time and that may eventually damage the hand dryer assembly. For example, the restricted air flow caused by an old filter may cause the hand dryer assembly to overheat leading to failure of the electric motor or heating element. Fifth, as air movement is restricted through a dirty filter, the blower assembly may find ways to pull air around the filter instead of through the filter. Sixth, the filter blocks the free movement of the moving air stream so the blower assembly typically must be uprated to provide the additional suction necessary to pull the desired velocity and volume of moving air stream through the filter. Accordingly, such hand dryer assemblies typically have poorer performance and are less energy efficient.

Another problem with hand dryer assemblies that employ a filter to clean the moving air stream is that the filter may be largely ineffective. The applicant has found that for hand dryers employing a filter that while the moving air stream air that exits the nozzle is generally filtered, the air that hits the user's hands is less so. More specifically, the moving air stream pulls in ambient air after the moving air stream exits the air outlet of the hand dryer assembly. Since the moving air stream includes ambient, entrained air that does not pass through the hand dryer assembly or the filter contained therein, the filter does not significantly reduce the particles or microorganisms relative to filterless hand dryer assemblies.

Another issue with many current hand dryer assemblies, particularly high-speed hand dryer assemblies, is that spray water from the drying of the user's hands may accumulate on surrounding surfaces of the hand dryer assembly and the support structure such as the walls and floor of the washroom. This errant spray may carry microorganisms from the ambient air or poorly washed hands of the user and thereby contaminate and grow on these surfaces. Accordingly, what is needed is a hand dryer assembly that sanitizes the moving air stream, the hands of the user, and surrounding surfaces of the hand dryer assembly and/or the washroom.

SUMMARY OF THE INVENTION

The present invention is generally directed to a hand dryer assembly for drying the hands of a user. The hand dryer generally may include an outer shell and a blower assembly disposed within the outer shell for generating a moving air stream. The hand dryer assembly includes an air outlet for discharging the moving air stream from the hand dryer assembly into ambient air disposed outside the outer shell. An air channel extends through the blower assembly and to the air outlet. Thus, the air channel communicates the moving air stream through the hand dryer assembly and to the air outlet. An ionization assembly is disposed along the air channel, preferably proximate to the nozzle, and more preferably with the nozzle. The ionization assembly includes at least two ion sources that emit charged ions directly into the moving air stream. The charged ions in the moving air stream are capable of sanitizing the hands of the user, the moving air steam, the ambient air that is entrained into the moving air stream after the moving air stream exits the air outlet, and various surrounding surfaces including surfaces of the hand dryer assembly and proximate walls and floors of the washroom. Since the charged ions have a short lifetime before combining with other molecules and losing their charge, the ionization assembly is designed to quickly transport the charged ions to the hands of the user and to be proximate to the outlet nozzle.

According to another aspect of the present invention, the ionization assembly includes a plasma power supply electrically connected to a power source. The power source, which may be a controller, supplies electricity of a pre-determined voltage to the hand dryer assembly. The plasma power supply then receives the electricity of the pre-determined voltage from the power source and generates electricity having a voltage that is greater than the pre-determined voltage of the electricity supplied by the power source. In other words, the plasma power supply steps up or increases the voltage of the electricity supplied by the power source of the hand dryer assembly. The high voltage electricity from the plasma power supply is then supplied to the ion sources where a voltage difference produced between the ion sources generates the charged ions.

According to another aspect of the present invention, the ion sources of the ionization device may be at least one pair of carbon brushes being oppositely charged and electrically connected to the plasma power supply to receive electricity from the plasma power supply and emit charged ions of opposite charges into the moving air stream. Each carbon brush may present a single or pointed end or alternatively may present a plurality of bristles with each bristle including a base and a pointed end for stripping electrons from the electricity generated by the plasma power supply. As electrons flow from the base to the pointed end of each bristle, the electrons are discharged into the moving air stream as charged ions.

According to yet another aspect of the present invention, the ionization assembly includes a brush holder supporting the at least one pair of carbon brushes in a substantially aligned and spaced relationship with respect to one another. Moreover, the brush holder may be mounted along the air channel to support the pair of carbon brushes transverse to the moving air stream such that the pair of carbon brushes extend substantially transverse to a flow direction of the moving air stream. Additionally, the brush holder may be located proximate to the air outlet such that the moving air stream need only carry the charged ions a short distance before impacting the hands of the user. The brush holder may also be configured to hold the carbon brushes in a spaced apart arrangement where the carbon brushes have a center-to-center distance ranging between about 18 millimeters and 23 millimeters, and more particularly and center-to-center distance equaling approximately 20 millimeters.

Advantageously, it has been found that this transverse arrangement and spacing of the carbon brushes introduces the greatest concentration of charged ions into the moving air stream and to the hands of the user without an attendant and undesirable production of ozone.

Accordingly, the advantages of the present invention are many. By providing a hand dryer assembly complete with an ionization assembly, a more sanitary hand dryer assembly and more particularly a more sanitary air stream is provided with less drawbacks than the state of the art hand dryer assemblies which utilize HEPA filters. Unexpectedly, the hand dryer assembly of the present invention is more effective than HEPA filters at reducing the amount of active microorganisms introduced to the user's hands during the drying operation even without any filtering of the air stream because the charged ions sanitize (1) the moving air stream expelled by the hand dryer assembly, (2) the ambient air that is entrained in the moving air stream once it exits the air outlet of the hand dryer assembly, and (3) even the user's hands. This is highly beneficial because it has been found that much of the air that hits the user's hands is ambient air that has been entrained by the moving air stream and HEPA filters are limited to filtering only the air that passes through the filter and dryer. The hand dryer assembly of the present invention is also essentially maintenance free and does not require filters, eliminating frequent filter replacement servicing, although optional filters may be added. This allows elimination of the cost and downtime associated with filter replacement. Additionally, the hand dryer of the present invention does not degrade in performance over time as there is no filter to become clogged and restrict air flow. The hand dryer of the present invention is also more energy efficient because the energy consumed by the ionization device has been found to be substantially less than the additional energy required to draw the moving air stream through a filter, particularly a HEPA filter, particularly a filter with trapped particles, as compared to a similar filter-less hand dryer assembly.

Another unexpected advantage of the hand dryer assembly of the present invention is that the charged ions emitted by the ionization assembly effectively sanitize the hands of the user as well as the surfaces of the hand dryer assembly and even to some degree the support structure and floor near the hand dryer assembly. It has been found that the charged ions kill microorganisms that have accumulated on surfaces just as proficiently as any airborne microorganisms that are pulled in through the air inlet. This is an advantage over prior art hand dryer assemblies because HEPA filters can only address airborne microorganisms in air that passes through the filter. This is also an advantage over prior art HVAC systems that employ ionization tubes. In these HVAC systems, the charged ions generated by the ionization tubes serve only to sanitize or purify the air within these systems and do not sanitize surfaces outside of the HVAC system because all of the charged ions will have combined with molecules by the time they would be expelled into the ambient air and out of the HVAC ductwork.

The ionization assembly of the present invention also represents an improvement over the prior art ionization tubes, thus enabling the use of the ionization assembly in the hand dryer assembly of the present invention. The size of the ionization assembly of the present invention is much smaller than prior art ionization tubes and is also much more durable. This size and durability improvement allows for the fitting of an ionization assembly into a hand dryer assembly. The lack of durability of the glass tubes used in HVAC was also a problem as many hand dryer assemblies must be vandal resistant given their use in public facilities, prisons, high crime areas, and the like. The ionization assembly of the present invention not only is very durable and reliable in harsh conditions, it also introduces a higher concentration of charged ions into the moving air stream than traditional ionization tubes thus satisfying the requirements of sanitizing the high velocity, low volume moving air stream of the hand dryer assembly all while generating no ozone. Another added benefit is that the charged ions also combine with airborne water molecules in the moving air stream or on the hands of the user and thus may dry, or reduce the humidity of, the moving air stream and provide quicker drying of the hands. Finally, the plurality of bristles presented on the carbon brushes of the ionization assembly provide for the additional benefit of reduced fouling by airborne dirt and dust as compared to an ionization assembly that presents only a single pointed end since airborne dirt and dust may foul the single pointed end preventing it from efficiently generating charged ions. In accordance with the present invention, the carbon brushes each include a plurality of bristles to present many pointed ends which has been found to reduce the chance of fouling.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 28 is a bottom elevational view of the backplate shown in FIG. 22;

FIG. 29 is a perspective view of another ionization assembly which may be placed within the hand dryer assemblies shown in FIG. 1 and FIG. 4;

FIG. 30 is an exploded perspective view of the ionization assembly shown in FIG. 29;

FIG. 31 is an exploded perspective view of another ionization assembly which may be placed within the hand dryer assemblies shown in FIG. 1 and FIG. 4;

FIG. 32 is a side elevational view of the ionization assembly shown in FIG. 31;

FIG. 33 is an enlarged elevational view of the base of the ionization assembly shown in FIG. 29.

DESCRIPTION OF THE ENABLING EMBODIMENT

Figure 1:
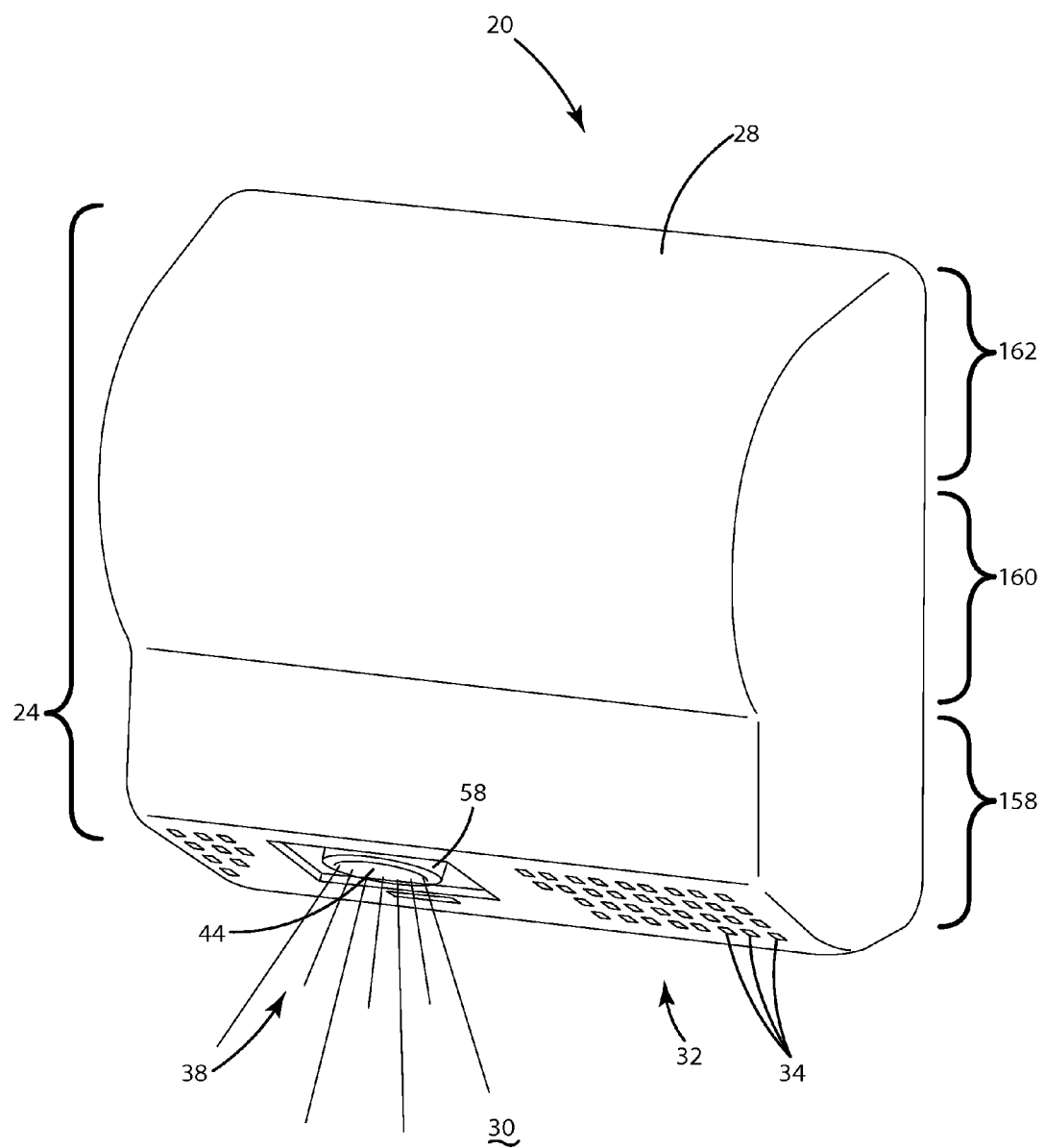
FIG. 1 is a front perspective view of an exemplary hand dryer assembly of the subject invention.

Referring to the Figures, wherein like numerals indicate corresponding parts throughout the several views, a hand dryer assembly 20 for mounting on a support structure 22 and for drying the hands of a user is disclosed.

As illustrated in FIGS. 1-28, the hand dryer assembly 20 has a housing 24 including a backplate 26 and an outer shell 28. The backplate 26 is configured to mount against the support structure 22. Typically, the support structure 22 is the wall of a washroom where users use the hand dryer assembly 20 to dry their hands after washing them. An outer shell 28 is attached to the backplate 26 of the hand dryer assembly 20. Generally, many of the components of the hand dryer assembly 20 are disposed within the housing 24. Surrounding the outer shell 28 is ambient air 30. The outer shell 26 includes an air inlet 32 for receiving the ambient air 30 disposed outside of the outer shell 28. More particularly, air inlet 32 may be a plurality intake vents 34 disposed in the outer shell 28. Thus, the air inlet 32 allows for the communication of ambient air 30 into the outer shell 28.

A blower assembly 36 is disposed within the outer shell 28 of the hand dryer assembly 20 for generating a moving air stream 38. The blower assembly 36 includes a blower fan 40 and an electric motor 42. The electric motor 42 is coupled to the blower fan 40 to drive the blower fan 40 at high rotational speeds to produce the moving air stream 38. Generally, the moving air stream 38 generated by the blower assembly 36 has a velocity or air speed of at least 10,000 linear feet per minute (LFM) and a volume flow rate of less than 100 cubic feet per minute (CFM) as measured at an air outlet 44 of the hand dryer assembly 20. A blower support 46 connects the electric motor 42 and the blower fan 40 to the backplate 26 of the hand dryer assembly 20. A blower housing 48 is mounted to the blower support 46 and surrounds at least part of the electric motor 42 and/or the blower fan 40. The blower housing 48 includes an inlet window 50 and an outlet window 52. The inlet window 50 is in fluid communication with the air inlet 32 of the outer shell 28 and functions to draw ambient air 30 into the outer shell 28 and the blower assembly 36. The outlet window 52 functions to expel the moving air stream 38 from the blower assembly 36. A heating element 54 is optionally disposed in the blower housing 48 adjacent the outlet window 52 for heating the moving air stream 38 as it exits the blower housing 48. The blower assembly 36 may further include an inlet shield 56 attached to the blower housing 48 and disposed over the inlet window 50. As such, the inlet shield 56 includes a plurality of holes for communicating air to the inlet window 50 and serves to prevent objects such as wires disposed within the outer shell 28 from becoming sucked into the inlet window 50 and impacted by the blower fan 40.

Figure 2:
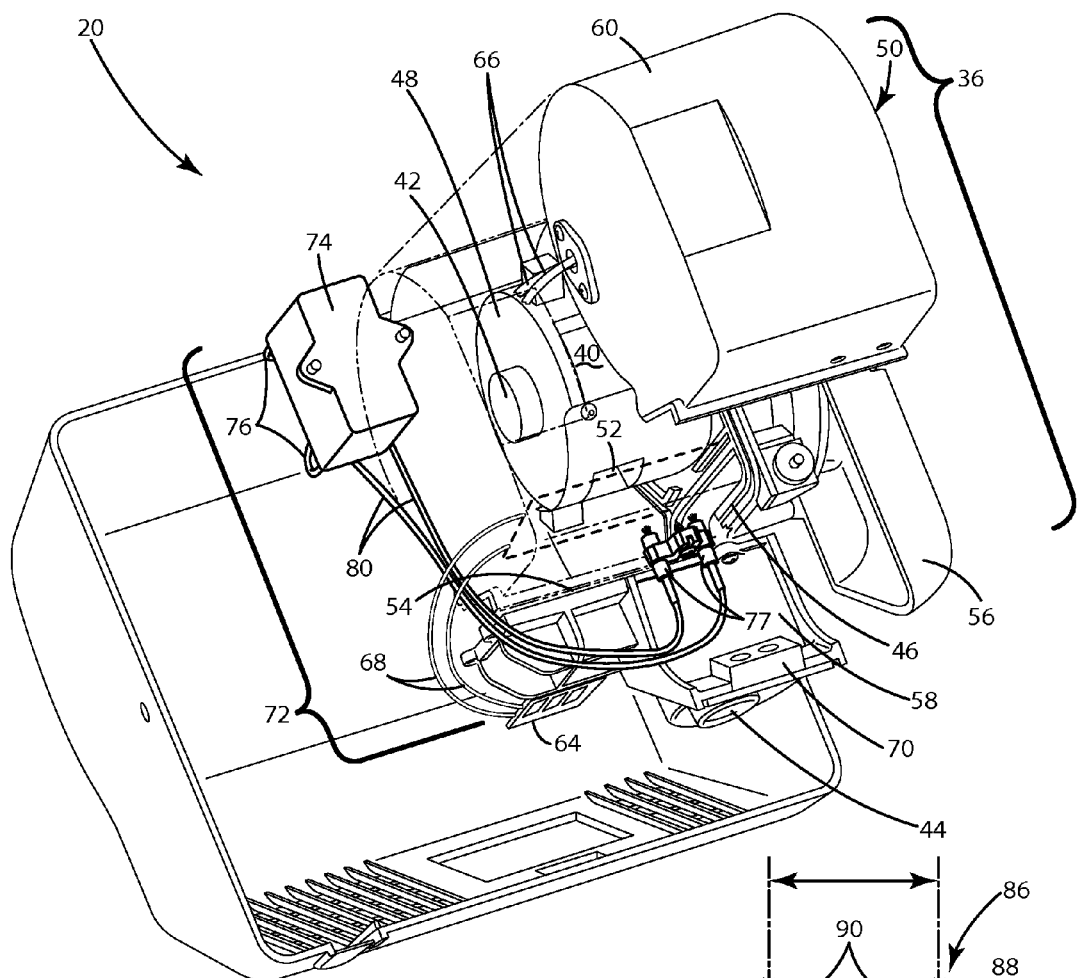
FIG. 2 is a partial exploded view the hand dryer assembly shown in FIG. 1 and further illustrates an exemplary ionization assembly mounted adjacent a blower assembly.
Figure 6:
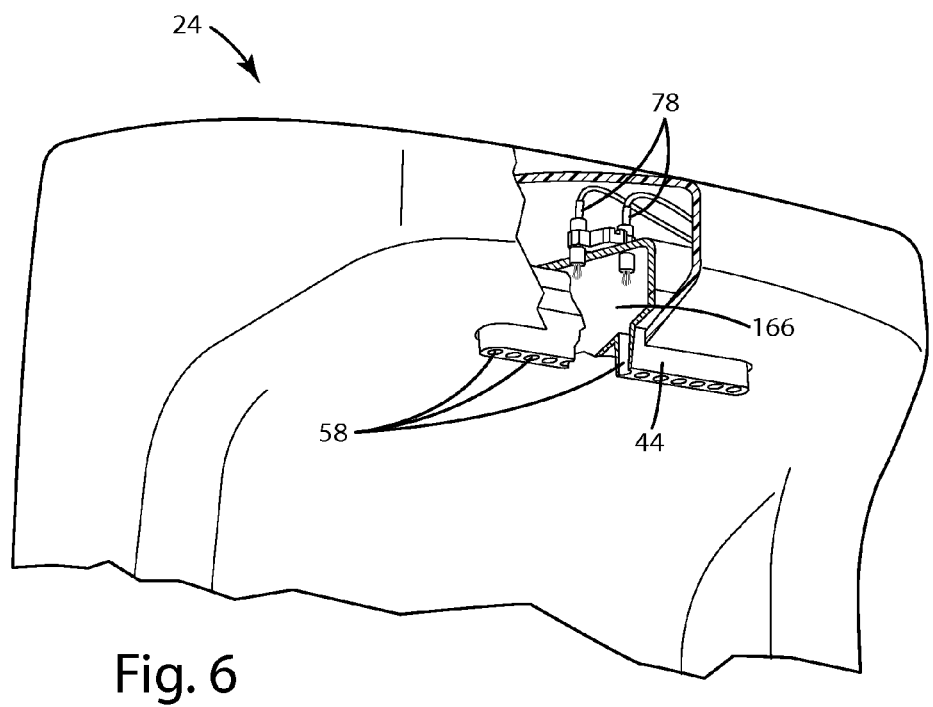
FIG. 6 is a partial sectional view of the upper portion of the hand dryer assembly shown in FIG. 4 and further illustrates an exemplary ion source mounted in an air channel adjacent to the nozzle.
Figure 7:
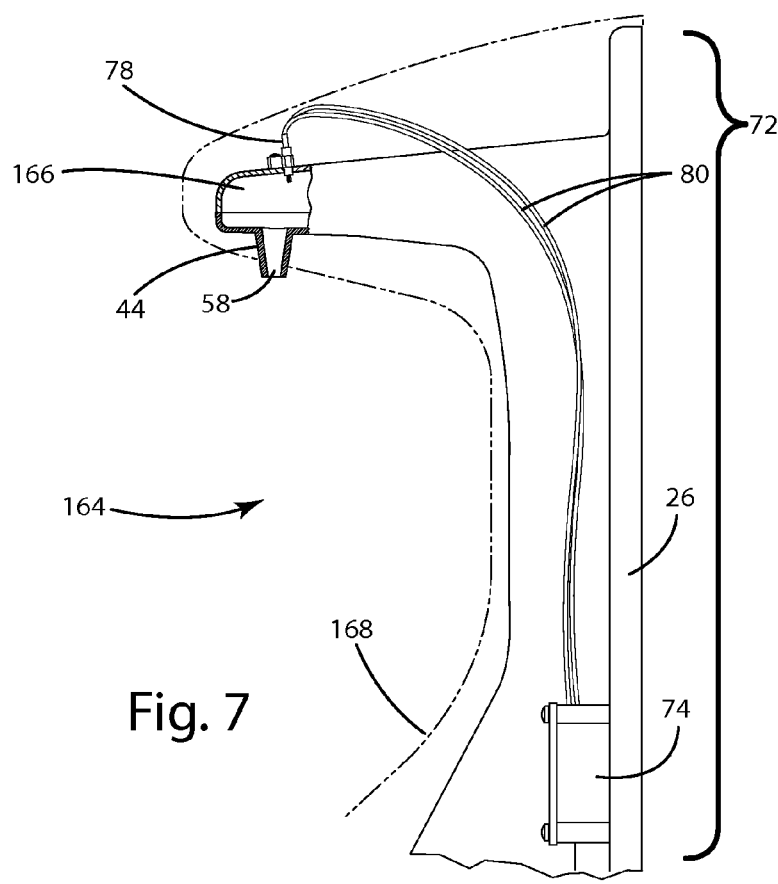
FIG. 7 is a partial cross-sectional view of the upper and middle portions of the hand dryer assembly shown in FIG. 4 taken along lines 7-7 and further illustrates the exemplary ion source mounted in the air channel.
Figure 8:
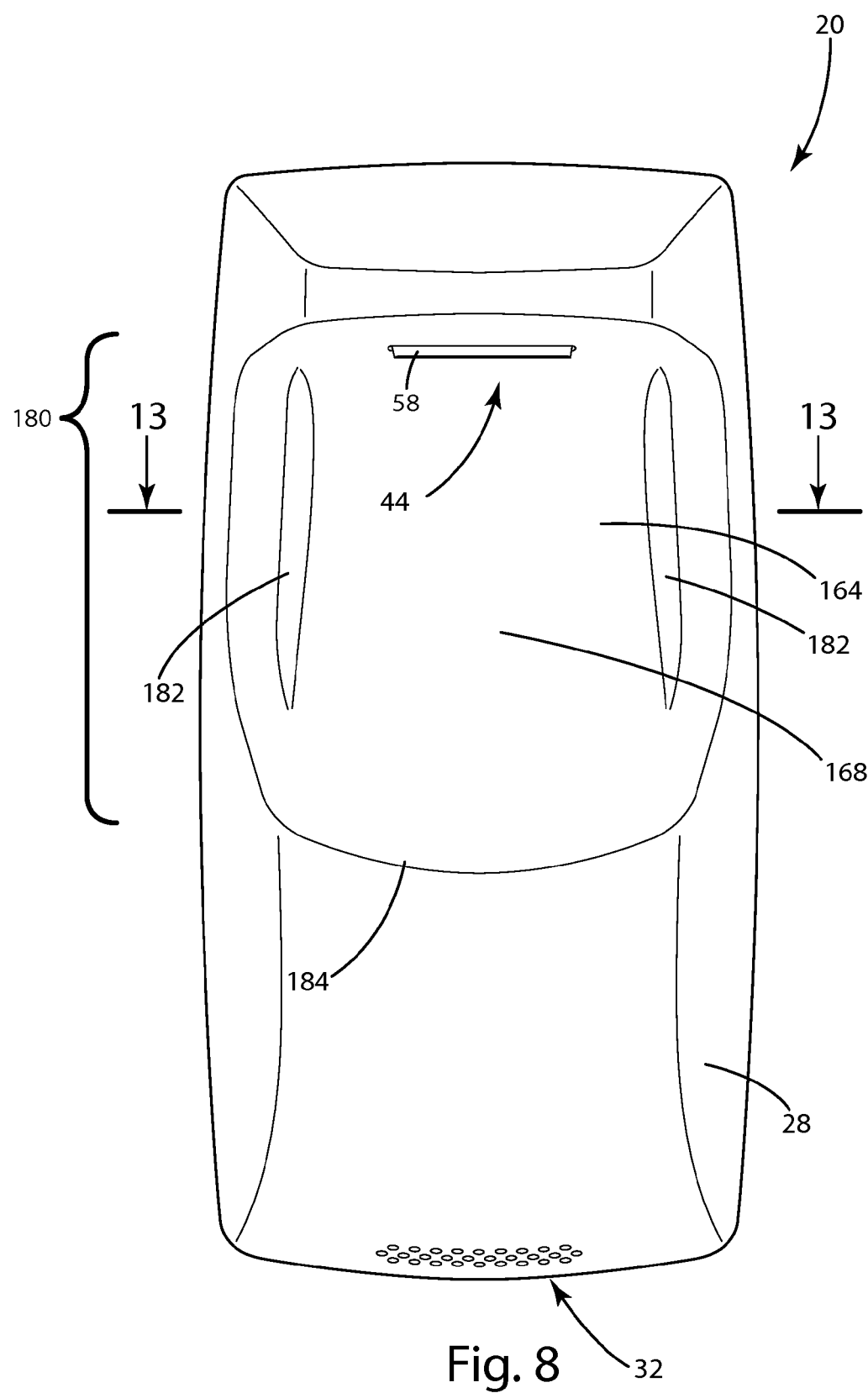
FIG. 8 is a front elevational view of the hand dryer assembly shown in FIG. 4.
Figure 14:
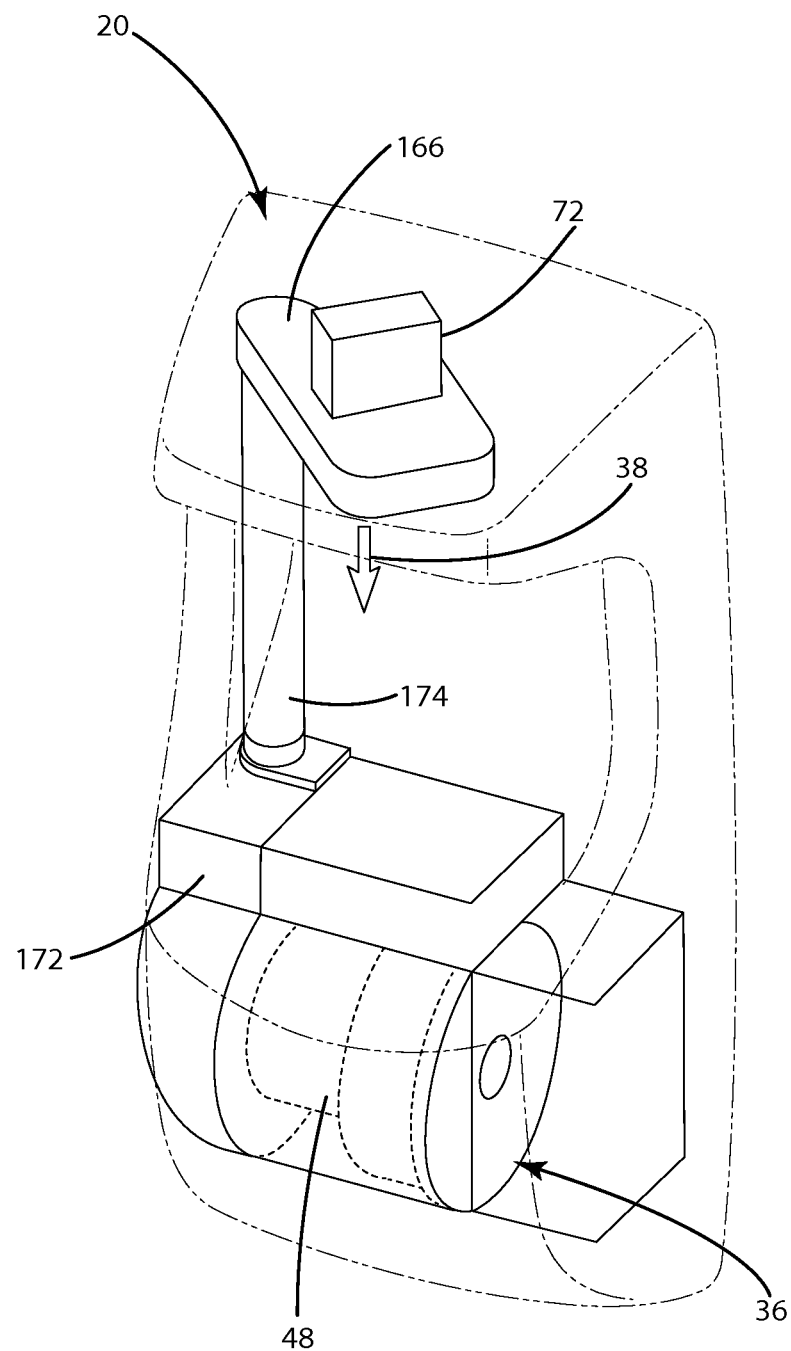
FIG. 14 is a front perspective view of the hand dryer assembly shown in FIG. 4 and further illustrates the air channel disposed within the housing.
Figure 15:
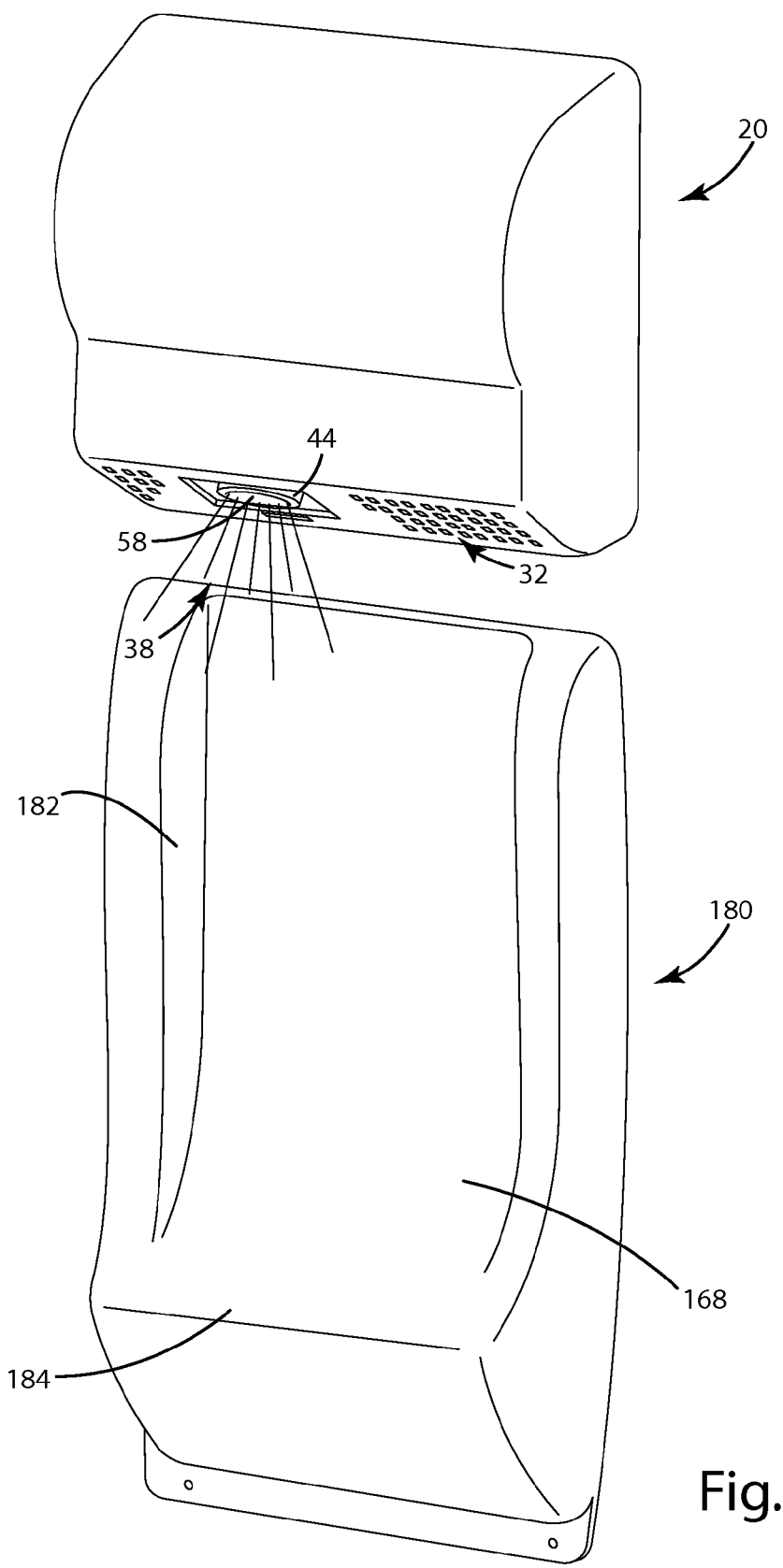
FIG. 15 is a front perspective view of the hand dryer assembly shown in FIG. 1 and a splash guard mounted to the support structure below the hand dryer assembly.
Figure 16:
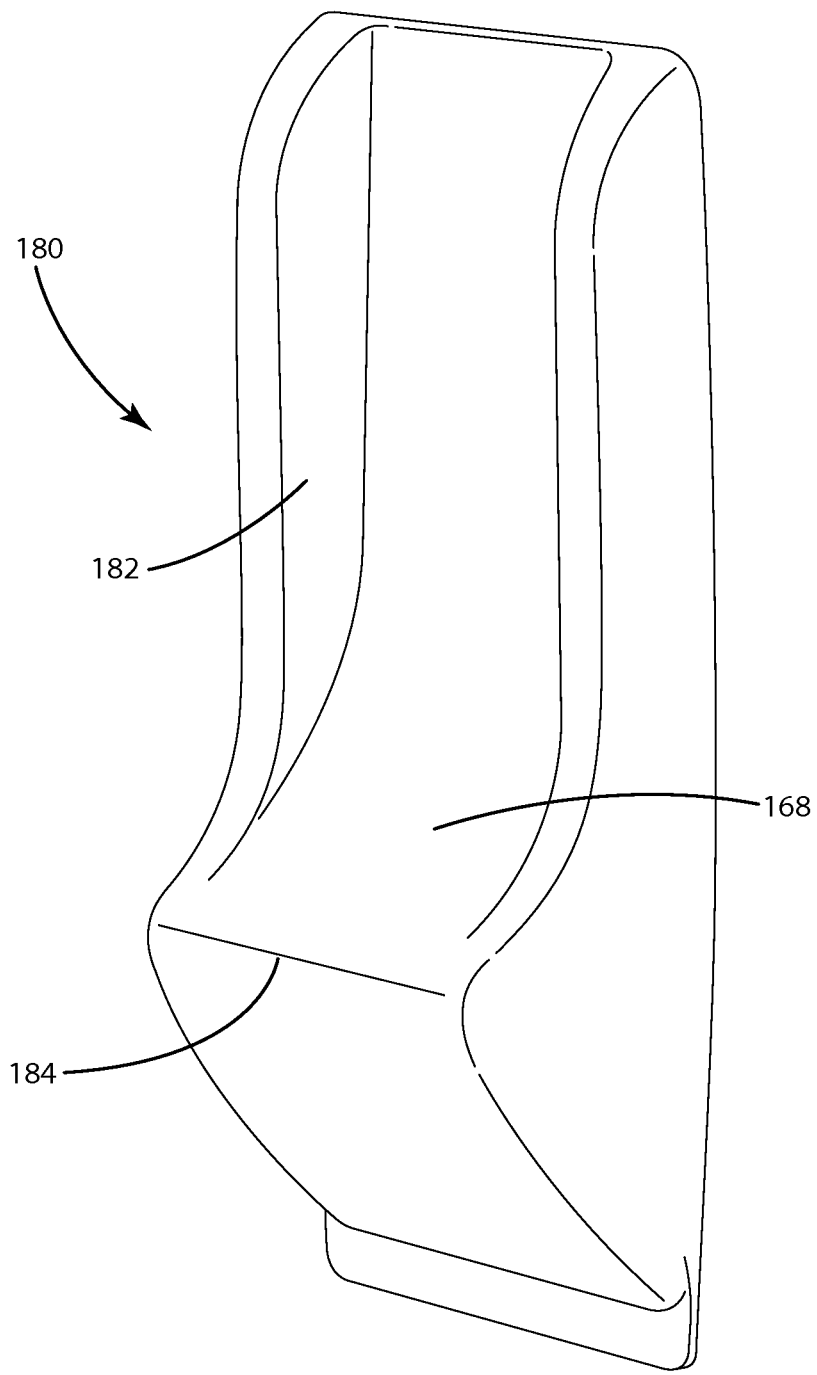
FIG. 16 is a front perspective view of the splash guard shown in FIG. 15.
Figure 17:
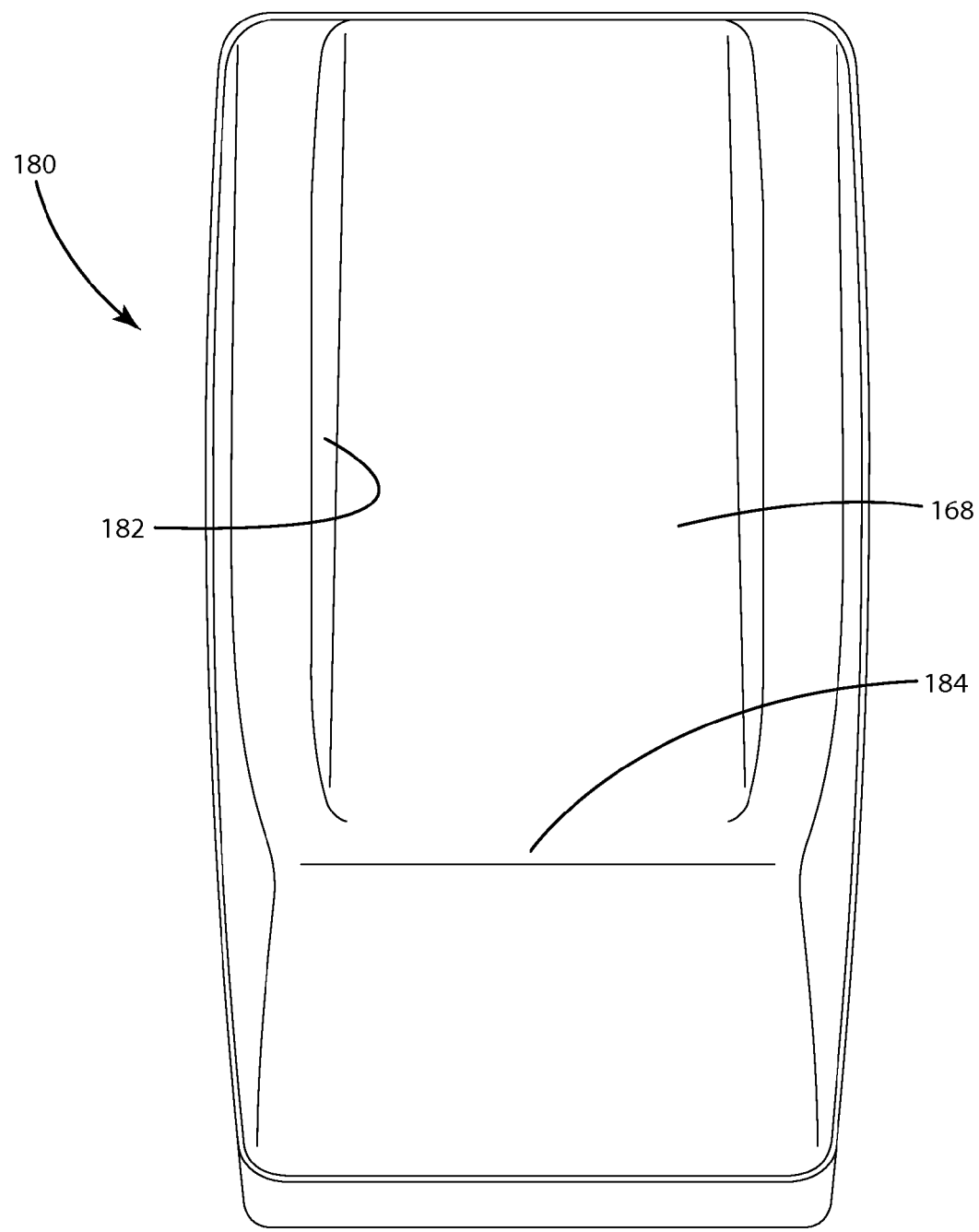
FIG. 17 is a front elevational view of the splash guard shown in FIG. 15.
Figure 18:
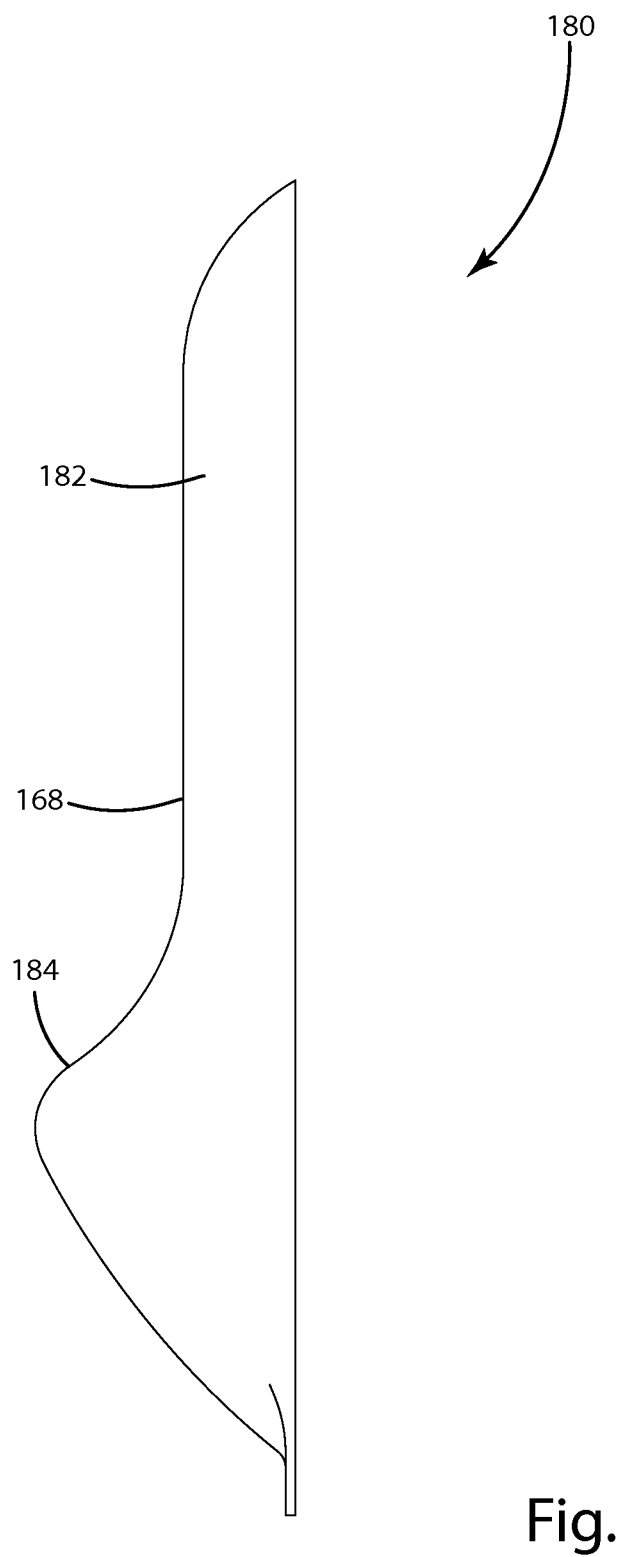
FIG. 18 is a side elevational view of the splash guard shown in FIG. 15.
Figure 19:
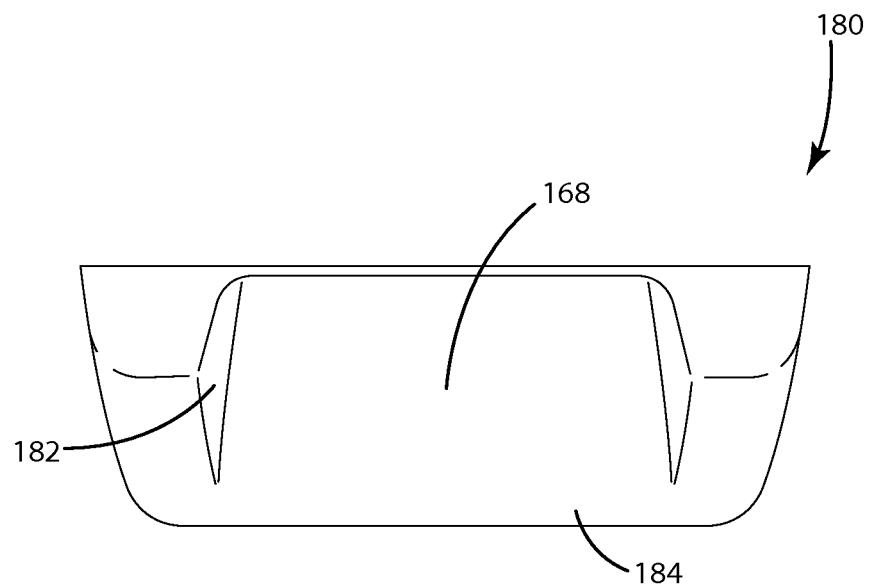
FIG. 19 is a top elevational view of the splash guard shown in FIG. 15.
Figure 20:
FIG. 20 is a bottom elevational view of the splash guard shown in FIG. 15.

A nozzle 58 of annular shape as illustrated in FIGS. 2 and 6 extends through the outer shell 28 of the hand dryer assembly 20. The nozzle 58 may have any desired size, shape, or configuration. The nozzle 58 includes the air outlet 44 which discharges the moving air stream 38 from the hand dryer assembly 20 into the ambient air 30 disposed outside the outer shell 28. The air outlet 44 may be a single opening or a plurality of openings each discharging at least a portion of the moving air stream 38. A plenum 60 extends from the outlet window 52 of the blower housing 48 to the nozzle 58. As illustrated in FIGS. 2 and 14, the moving air stream 38 is communicated from the blower assembly 36 through the plenum 60 to the nozzle 58. Generally, the hand dryer assembly 20 includes an air channel 62. This air channel 62 defines a flow path for the moving air stream 38 through the hand dryer assembly 20 and may extend through one or more components of the hand dryer assembly 20. For instance, the air channel 62 may extend from the air inlet 32 and pass through the inlet window 50 of the blower assembly 36. From there, the air channel 62 may extend through the blower housing 48 and the outlet window 52 of the blower assembly 36. Finally, the air channel 62 may extend through the plenum 60 and the nozzle 58 to reach the air outlet 44.

Figure 5:
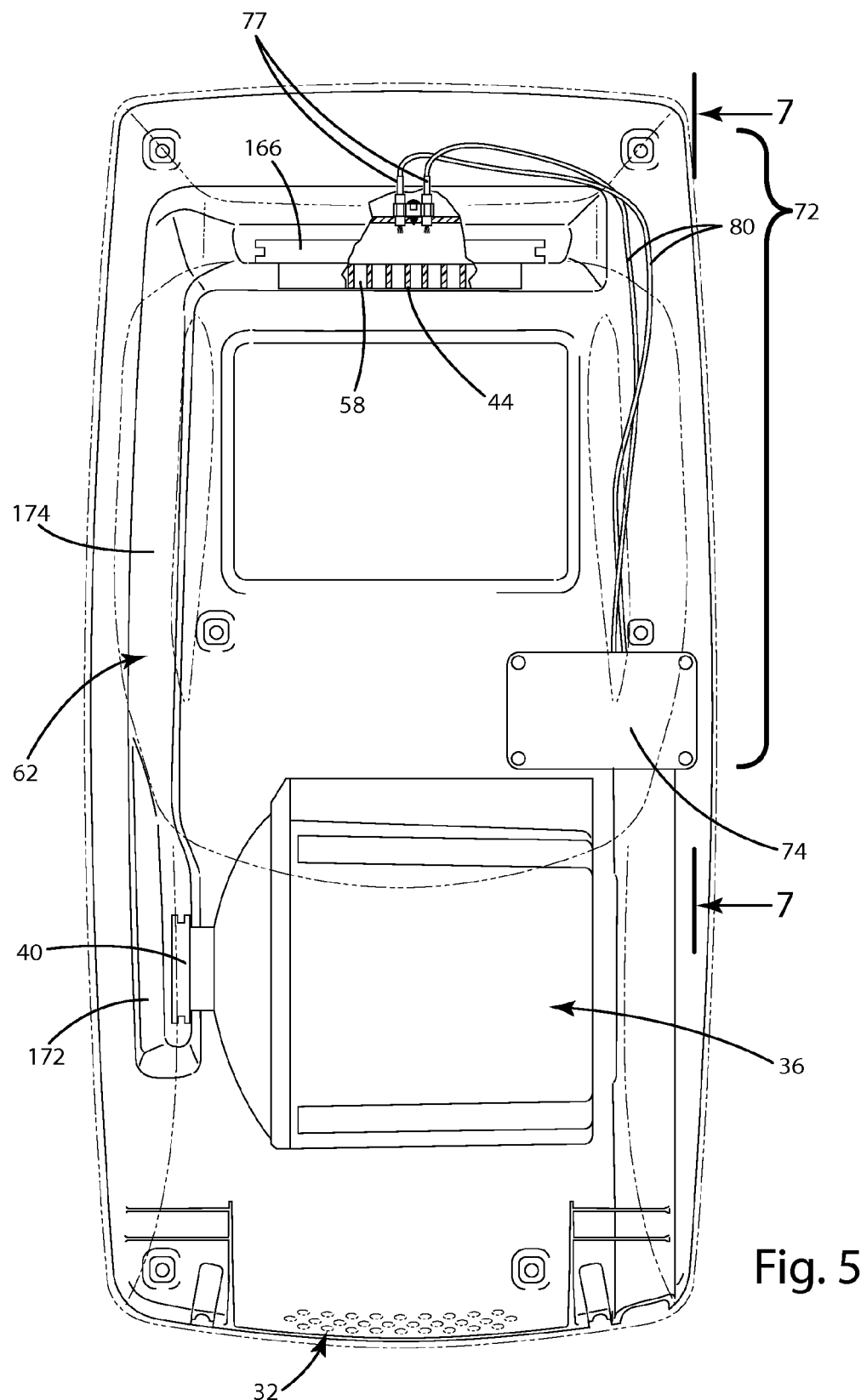
FIG. 5 is a partial sectional view of the hand dryer assembly shown in FIG. 4 and further illustrates an exemplary ionization assembly.

Referring to FIGS. 2 and 5, electricity is supplied to the blower assembly 36 by a power source 64 or a controller 64. It should be appreciated that the electricity has both voltage and current. Operation of the hand dryer assembly 20 may be governed by the controller 64. The controller 64 may be mounted to the backplate 26 of the hand dryer assembly 20 and is electrically connected to the electric motor 42 and optionally the heating element 54. The controller 64 supplies electricity of a pre-determined voltage to the electric motor 42 and optionally the heating element 54 of the blower assembly 36. Specifically, a pair of blower wires 66 are connected between the electric motor 42 and the controller 64 and a pair of heater wires 68 are optionally connected between the optional heating element 54 and the controller 64. Accordingly, the electric motor 42 drives the blower fan 40 and generates the moving air stream 38 in response to receiving electricity from the controller 64 through the pair of blower wires 66. The heating element 54 heats the moving air stream 38 in response to receiving electricity from the controller 64 through the pair of heater wires 68. While the heating element 54 could take many forms, the heating element 54, is optional and may employ electrical resistive heating to heat the moving air stream 38. The controller 64 is electrically connected to a motion sensor 70 that is mounted to the nozzle 58. The motion sensor 70 activates the controller 64 in response to detecting the presence of the hands of the user adjacent the nozzle 58. It should be appreciated that the term motion sensor 70 as used herein is meant to include any sensor capable of detecting the presence of the hands of the user adjacent the nozzle 58 regardless of whether the detection requires movement of the hands. Alternatively, the controller 64 may be activated by a push button or switch (not shown) mounted to the outer shell 28 of the hand dryer assembly 20. Alternatively, the controller 64 and blower assembly 36 may be programmed to disperse ionized particles and air at a lower rate and continuously between user activation phases.

Charged ions can be used to kill airborne microorganisms and remove airborne odors and pollutants. As such, it would be desirable to produce a hand dryer assembly 20 that generates charged ions and transports them to the hands of the user and surrounding surfaces to sanitize the same. However, existing devices capable of generating charged ions are not well suited for use in hand dryer assemblies 20. Prior ionization tubes used with HVAC systems utilize a cathode that is completely surrounded by a glass tube. The inside of the glass tube contains a wire mesh that serves as an anode. Charged ions are created in the spaced between the cathode and the glass tube due to the high voltage difference between the cathode and the anode disposed on the glass tube. Such ionization tubes do not suit the demands of hand dryer assemblies 20 for several reasons. First, glass by its very nature has a fragile structure and is prone to breaking. Hand dryer assemblies 20 are built to sustain impacts during their service life and the presence of a glass ionization tube would reduce the toughness of the hand dryer assembly 20. Second, the glass tube requires a voltage high enough to break down the dielectric strength of the glass which substantially increases the energy consumption of the ionization tube as compared to the present invention and makes use of such tubes as undesirable as typically only limited supply of power available for one blower as well as the heating element. Third, when the dielectric strength of the glass is broken down, corona discharge is created which produces significant ozone, a known health concern. Fourth, the glass tube breaks down over time and must be regularly replaced similar to incandescent light bulbs. The replacement cost for the glass tube is extremely high and may require major disassembly for replacement. Fifth, the concentration of charged ions produced by these glass ionization tubes is not sufficient for the higher velocity air stream produced by hand dryer assemblies 20. HVAC systems generally have an air stream velocity of less than 2,000 linear feet per minute (LFM) and/or a volume flow rate that is greater than 400 cubic feet per minute (CFM). By contrast, hand dryer assemblies 20 have a much greater air stream velocity and require a much higher concentration of charged ions to effectively sanitize the quickly moving air stream and the hands of the user. Finally, the size and shape of the glass ionization tube does not fit well within the compact packaging of a hand dryer assembly 20. All of these obstacles counseled against the feasibility of fitting an ionization tube within a hand dryer assembly 20.

The present invention presents a hand dryer assembly 20 that includes an ionization assembly 72 that is compact, durable, energy efficient, and capable of introducing a high concentration of charged ions directly into the moving air stream of the hand dryer without any associated ozone production. The hand dryer assembly 20 beneficially sanitizes the moving air stream 38, the hands of the user, and surrounding surfaces of the hand dryer assembly 20 and/or the washroom.

Referring to FIGS. 2 and 5-7, the hand dryer assembly 20 disclosed provides an ionization assembly 72 disposed along the air channel 62. The ionization assembly 72 emits charged ions directly into the moving air stream 38 to sanitize the moving air stream 38 as well as the hands of the user. As such, the moving air stream 38 quickly transports charged ions to the hands of the user which act to kill microorganisms including harmful viruses and bacteria. For example testing has shown that the charged ions produced by the ionization assembly 72 of the disclosed hand dryer assembly 20 kill over 99% of *E. coli* bacteria (a common washroom microorganism) within the normal operation cycle of the hand dryer assembly 20. In a similar fashion, the ionization assembly 72 also sanitizes the moving air steam 38 and the ambient air 30 that is entrained into the moving air stream 38 after the moving air stream 38 exits the air outlet 44. This is important because a significant amount of the air that impacts the hands of the user is not the moving air stream 38 discharged through the air outlet 44 of the hand dryer assembly 20 but instead is ambient air 30 that has been entrained into the moving air stream 38. The ionization assembly 72 may also sanitize any surface of the hand dryer assembly 20 and/or the support structure 22 that is impacted by the moving air stream 38 and/or the entrained ambient air 30, such as the support structure 22 including the walls and floor proximate to the hand dryer assembly 20. Of course, as the distance from the hand dryer assembly 20 increases, the number of available charged ions decreases because the charged ions react with the molecules in the ambient air. However, it has been found that the repeated cycling of the hand dryer through multiple users over time provides enough ions to effectively sanitize the surrounding support structure and other surfaces across which the continued use occurs.

The ionization assembly 72 of the hand dryer assembly 20 includes a plasma power supply 74. The plasma power supply 74 is mounted to the backplate 26 and is electrically connected to the controller 64 by a pair of power leads 76. The power leads 76 may directly connect to and receive electricity from the pair of blower wires 66. Regardless, the plasma power supply 74 receives electricity from the controller 64 and generates a voltage that is greater than the pre-determined voltage of the electricity supplied by the controller 64. In other words, the plasma power supply 74 receives electricity of the pre-determined voltage from the controller 64 as an input. The plasma power supply 74 then steps up or increases the voltage of the electricity supplied by the controller 64. As a result of this voltage step up or increase, the plasma power supply 74 outputs electricity that has a voltage that is greater than the pre-determined voltage of the electricity supplied by the controller 64. Accordingly, the plasma power supply 74 acts as a voltage regulator or voltage conditioner which increases the voltage of the electricity it receives from the controller 64 without changing the current. It should be appreciated that the current of the electricity depends on the load of the ionization assembly 72.

Figure 3:
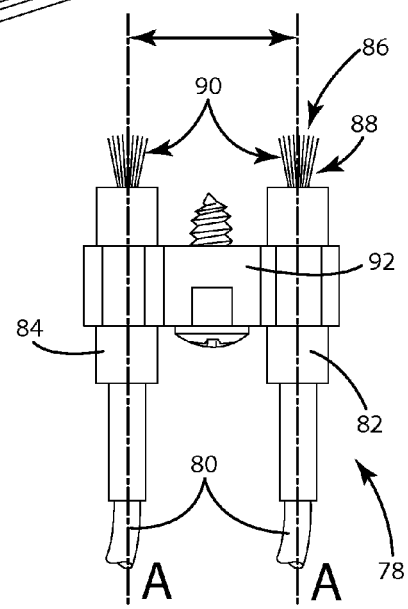
FIG. 3 is a side elevational view of an exemplary ion source of the ionization assembly in FIG. 2.
Figure 4:
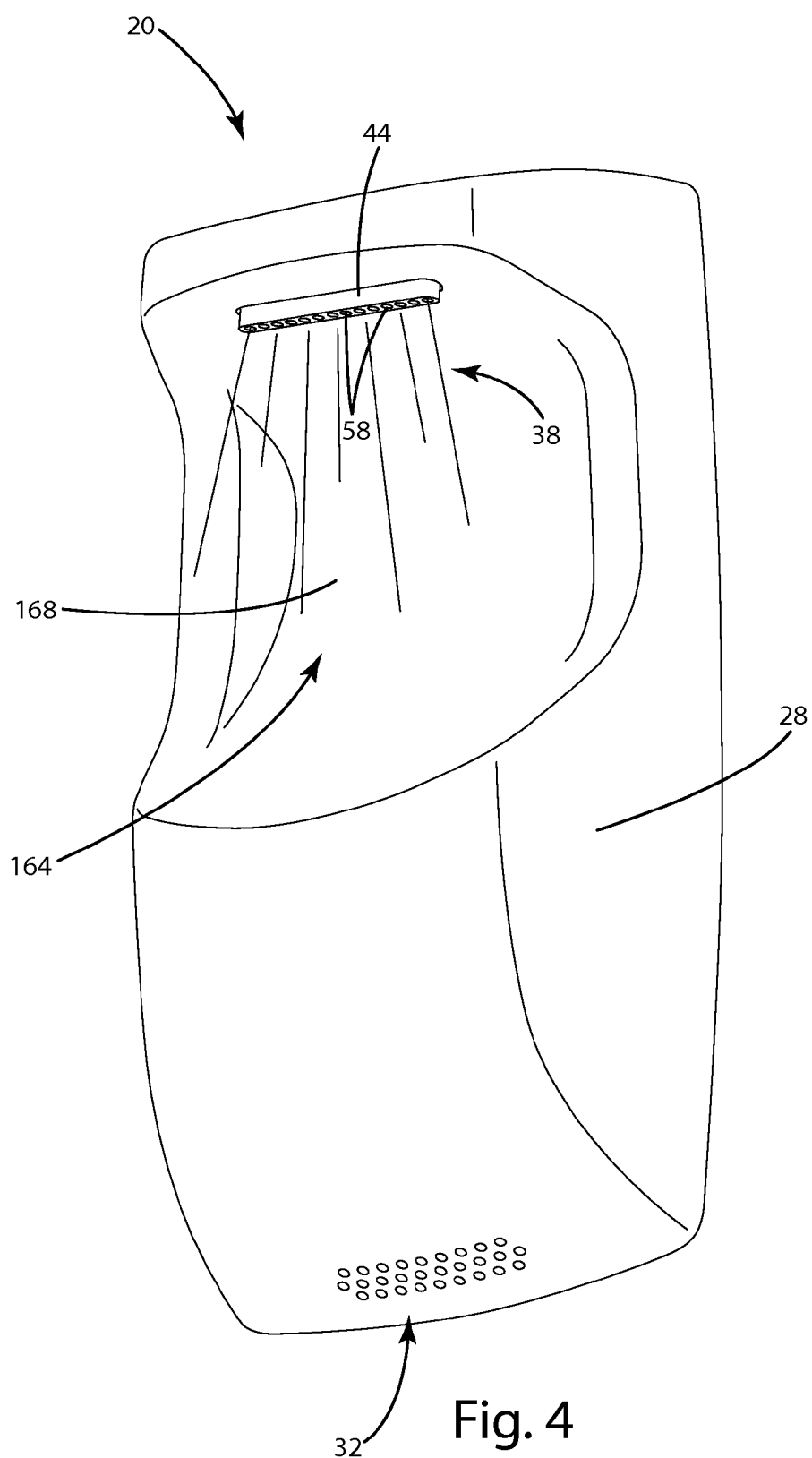
FIG. 4 is a front perspective view of another exemplary hand dryer assembly of the subject invention.

The ionization assembly 72 may further include at least two ion sources 77. Referring to FIG. 3, the ion sources 77 may be at least one pair of carbon brushes 78 and may be electrically connected to the plasma power supply 74 by a pair of high voltage leads 80. The pair of carbon brushes 78 may be placed in the moving air stream 38 proximate to the nozzle 58. The pair of carbon brushes 78 receive electricity from the plasma power supply 74 via the pair of high voltage leads 80, and as a result, the carbon brushes emit charged ions into the moving air stream 38. It should be appreciated that at any given time, one of the ion sources 77 act as a cathode 82 while the other of the ion sources 77 act as an anode 84 such that a voltage differential is maintained between the two. In some circumstances, the charged ions may only be emitted from only one of the ion sources 77 and depending on the voltage supplied those ions may be positively charged or negatively charged. It should also be appreciated that the electricity produced by the plasma power supply 74 may be direct current (DC) electricity where the charges of the carbon brushes 78 are opposite and remain the same or alternating current (AC) electricity where the pair of carbon brushes 78 are oppositely charged for a given time value but where the charge of each carbon brush 78 alternates. In other words, the ionization assembly 72 may be classified as a bipolar ionization device. As such, it should be appreciated that the ionization assembly 72 may simultaneously generate charged ions of opposite charges (positive and negative charges). Each carbon brush 78 of the pair of carbon brushes 78 may alternate between being positively charged and negatively charged with time. Accordingly, the each carbon brush 78 may switch between being the cathode 82 (positively charged) and the anode 84 (negatively charged). Thus, the charged ions emitted by the pair of carbon brushes 78 include both positively charged ions and negatively charged ions. Switching the charges has also been found to reduce unequal buildup of dust on one of the brushes. While the present invention does not need filters, it has been found that a filter prevents dust buildup on the brushes and therefore improving the long term efficiency of the carbon brushes 78.

The ion sources 77 of the ionization assembly 72 may each present a single pointed end 86 and a base 88. Alternatively, where the ion sources 77 are carbon brushes 78, each brush 78 also each present a plurality of bristles 90. Each bristle 90 of the plurality of bristles 90 may include the bristle base 88 and a bristle end 86 and may be made of one or more carbon fibers. While carbon fibers have been found to work well, other materials with similar electrical conductivity characteristics may be submitted. For example, stainless steel needles have been found to be a suitable material. Thus, the bristles 90 of the ion sources 77 may be made of a material other than carbon. The plasma power supply 74, through the pair of high voltage leads 80, supplies electricity to the base 88 of each bristle 90 as a flow of electrons. As the electrons flow from the base 88 of the bristle 90 to the bristle end 86, electrons are stripped off and discharged into the moving air stream 38 as charged ions. This process occurs given the voltage differential between the ion sources 77. The pair of carbon brushes 78 are supported along the air channel 62 by a brush holder 92. As illustrated in FIG. 3, each of the carbon brushes 78 generally has a central axis A extending through the middle of the clump of bristles 90 and extending in the direction of their axial length. The brush holder 92 supports the carbon brushes 78 such that the central axis A of the carbon brushes 78 are substantially aligned. As the term is used herein, aligned means that the central axes A of the carbon brushes 78 generally extend in the same direction such that any angle between the central axes A is small. Preferably, the central axes A of the carbon brushes 78 are parallel and spaced apart from one another. The brush holder 92 may be mounted to the plenum 60 and may support the pair of carbon brushes 78 transverse to the moving air stream 38 such that the central axes A of the carbon brushes 78 extend substantially transverse to a flow direction of the moving air stream 38. Thus, the ion sources 77 extend through the plenum 60 and at least partially into the air channel 62.

The spacing of the carbon brushes 78 is important because when the center-to-center distance b between the carbon brushes 78 is small, arcing can occur between the pair of carbon brushes 78, which shortens the life of the pair of carbon brushes 78 and such arching also produces ozone. Ozone in certain quantities is toxic to humans over time so safety considerations generally require the ozone free operation of indoor appliances such as hand dryers. On the other hand, when the center-to-center distance b between the brushes is large, fewer charged ions are generated for a given level of electricity. With these considerations in mind, the inventor has found a center-to-center distance b between about 18 millimeters and 23 millimeters, and more particularly equal to 20 millimeters, as measured between the carbon brushes 78, to be optimal where arcing is eliminated while maintaining a sufficient concentration of charged ions emitted into the moving air stream 38 to achieve the desired sanitizing effect. Of course changes in the applied voltage may cause some changes in the spacing. As such, an electrical potential of 5,000 volts (V) and 0.5 milliamps (mA) is desired for such a spacing.

Referring now specifically to FIGS. 29-32, the ionization assembly 72 may alternatively be a generally bar shaped unit that is mounted within the air channel 62 of the hand dryer assembly 20. This contrasts the embodiment described above where the ion sources 77 extended through the plenum 60 to partially project into the air channel 62. The ionization assembly 72 may generally include base 94, the anode 84, the cathode 82, and a power input terminal 96. Where the ionization assembly 72 includes at least one pair of carbon brushes 78, each carbon brush 78 of the pair alternates being the anode 84 and the cathode 82 with the alternating current (AC) electricity provided by the plasma power supply 74. Alternatively, the anode 84 may be a generally cylindrical tube that extends from the base 94 between a bottom end 98 and a top end 100. The cathode 82 may be spaced apart from the anode 84 and may partially circumscribe the anode 84. A power input terminal 96 may be integrated with the anode 84 or may engage the anode 84. As illustrated in FIG. 30, the power input terminal 96 may extend through the base 94 and extend a distance from the base 94 for engaging the plasma power supply 74.

As illustrated in FIG. 29, the power input terminal 96 and the anode 84 may be integral, meaning the power input terminal 96 is formed from the anode 84. For example, the power input terminal 96 may be machined into the bottom end 98 of the anode 84. This may be done by turning the bottom end 98 of the anode 84 on a lathe. The power input terminal 96 has a top end 102 and a bottom end 104 and receives high voltage electricity from the plasma power supply 74. The power input terminal 96, as illustrated, may extend a distance away from the base 94 to allow for connection to the plasma power supply 74. As illustrated in FIG. 29, the power input terminal 96 may be directly screwed into the plasma power supply 74 for selectively securing the ionization assembly 72 to the plasma power supply 74.

The top end 100 of the anode 84 may present the ion sources 77 which may be a plurality of tines 105 or carbon brushes 78. The ion sources 78 may be embedded into bores 106 that are spaced along the axial length of the top end 100 of the anode 84. Where tines 105 are used for the ion sources 78, the base 88 of the tines 105 is larger than the pointed end 86. Preferably, the pointed end 86 of each tine 105 has a point. In other words, the tines 105 have a base 88 that is embedded into a bore 106 spaced along the axial length of the top end 100 of the anode 84 and the pointed end 86 of the tines 105 forms a point. The diameter of the tines 105 from the base 88 to the pointed end 86 gradually decreases until a point is formed. The tines 105 may be composed of stainless steel, gold, titanium, brass, or any other conductive, but oxidation resistant material.

The cathode 82 may be annular in shape and may partially circumscribe the anode 84. The diameter of the cathode 82 may be slightly larger than the diameter of the anode 84, thus providing a spaced apart relationship when the anode 84 is placed within the cathode 82. The term partially circumscribes is intended to mean that the cathode 82 does not fully encompass the anode 84. The cathode 82 has a first side and a second side that are not engaged, but are spaced apart. In one embodiment, the cathode 82 partially circumscribes the anode 84 at an angle of greater than 180 degrees with respect to the anode 84, but does not circumscribe the anode 84 at an angle of 360 degrees.

The base 94 of the ionization assembly 72 may be any type of insulated material that is capable of retaining the anode 84. As illustrated in FIGS. 29 and 30, the base 94 of the ionization assembly 72 may contain a mounting base 108 and a retention base 110. The mounting base 108 contains a bore 112 that extends through the center of the mounting base 108. The bore 112 may be threaded for receiving a correspondingly threaded portion of the bottom end 98 of the anode 84. Alternatively, the bore 112 may contain no threads and may allow the anode 84 to extend therethrough uninhibited. A correspondingly threaded nut 114 may be utilized to selectively secure the anode 84 to the base 94, and in particular the mounting base 108. The mounting base 108 may contain a top portion 116 and a bottom portion 118. The bottom portion 118 of the mounting base 108 may be threaded and the inside of the retention base 110 may contain corresponding threads for selectively securing the mounting base 108 to the retention base 110.

As illustrated in FIGS. 29 and 30, a conductive ring 120 may be engaged to the base 94. The conductive ring 120 may be disposed between the plasma power supply 74 and the retention base 110. The conductive ring 120 may further include a metal bracket 122 that circumscribes the cathode 82. A grounding wire 124 having a first end 126 and a second end 128 extend between the metal bracket 122 and the conductive ring 120 wherein the first end 126 is engaged to the metal bracket 122 and the second end 128 is engaged to the conductive ring 120. The first end 126 and the second end 128 of the grounding wire 124 may contain a circular metallic lead 130 with a central bore 132. The metal bracket 122 and conductive ring 120 may each contain a conductive screw 134 that is received within the central bore 132 of the metallic lead 130 on the first end 126 and the second end 128 of the grounding wire 124. A correspondingly threaded nut 114 may be disposed on the conductive screw 134 for retaining the grounding wire 124 to the conductive ring 120 and metal bracket 122. In lieu of the conductive ring 120 and metal bracket 122, the plasma power supply 74 may contain a grounded biasing element 136. The grounded biasing element 136 has a bottom portion and a top portion, wherein the bottom portion is engaged to the plasma power supply 74 and the top portion is engaged to the cathode 82.

The top of the cathode 82 may be retained in a spaced apart relationship to the anode 84 with a spacer 138. The spacer 138 may be composed of rubber or another electrically insulated material. That spacer 138 may have a circular body 140 with a raised shelf at one end. The spacer 138 may also contain a hollow bore 142 extending through the center of the spacer 138. The hollow bore 142 of the spacer 138 may have a diameter slightly larger than the diameter of the anode 84 for receiving the anode 84 into the hollow bore 142. The circular body 140 of the spacer 138 may have a diameter slightly smaller than the diameter of the cathode 82, allowing the cathode 82 to fit around the circular body 140 of the spacer 138. The spacer 138 is designed to receive a retention pin 144 that is received within an upper portion of the hollow bore 142 of the spacer 138 and selectively secures the anode 84 to the spacer 138.

The anode 84 may be composed of any material that can conduct electricity. For example, the anode 84 may be composed of brass or any other conductive, oxidation resistant material. The tines 105 can also be manufactured out of any material that conducts electricity such as tungsten or stainless steel. The cathode 82 may be manufactured from stainless steel or any other conductive, oxidation resistant material. It should be noted that the cathode 82 and anode 84 may be of various sizes depending upon the specifications and requirements of the hand dryer assembly 20. The ionization assembly 72 is inserted into the plenum 60 of the hand dryer assembly 20 so that the moving air stream 38 flows transverse to longitudinal length of the ion sources 77 on the anode 84. In other words, ionization assembly 72 should be positioned such that the ion sources 77 are upright in relation to the moving air stream 38 such that the moving air stream 38 is able to flow between the tines 105 or the carbon brushes 78.

During use, the plasma power supply 74 supplies electricity to the power input terminal 96. As a result, electrons flow along the length of the anode 84 and as the electrons progress from the power input terminal 96 along the anode 84 the electrons contact the ion sources 78 and flow up from the base 88 to the pointed end 86. When the electrons reach the pointed end 86 of the tines 105 or the bristles 90 of the carbon brushes 78, the electrons flow from the pointed end 86 of the tine 105 or bristle 90 of the anode 84 to the cathode 82 that may or may not partially circumscribes the anode 84. Not all of the electrons that flow from the anode 84 are collected by the cathode 82. Instead, the electrons that are not collected by the cathode 82 flow into the surrounding area and collide with air molecules and particles in the moving air stream 38, thus ionizing the air molecules and particles to generate the charged ions. The ionization of the moving air stream 38 functions to clean the moving air stream 38, remove odors, and reduce pollutants.

Referring to FIGS. 31 and 32, the ionization assembly 72 may also include a conductive portion 146 and a bar housing 148. The plasma power supply 74 may span the length of the ionization assembly 72. The conductive portion 146 also may span the length of the ionization assembly 72 and may be disposed in close proximity to the plasma power supply 74. The bar housing 148 may contain a cavity 150 for retaining the plasma power supply 74 and the conductive portion 146. Preferably, the bar housing 148 contains a back and two side portions extending from the back and forming the cavity 150 therein. The cavity 150 is designed to retain and protect the plasma power supply 74 and the conductive portion 146.

The conductive portion 146 may be made of any material that conducts electricity. For example, the conductive portion 146 may be composed of a thermoplastic polymer imbedded with conductive material that allows the polymer to conduct electricity. More specifically, the conductive portion 146 may be composed of polypropylene impregnated with carbon. However, any other resistive, inductive, reactive, or conductive plastic or nonmetallic material may be utilized for the conductive portion 146.

Again, the ionization assembly 72 may include a plurality of ion sources 77 such as tines 105 or carbon brushes 78. The ion sources 77 may be disposed on the conductive portion 146 and may be embedded into the bores 106 that are spaced along the axial length of the top of the conductive portion 146. The bases 88 of the ion sources 77 may also be integral with the conductive portion 146 and spaced along the axial length of one side of the conductive portion 146.

As illustrated in FIGS. 31 and 32, an extrusion 152 may be positioned between the plasma power supply 74 and conductive portion 146 and the bar housing 148. The extrusion 152 may be made of a non-conductive material so that the extrusion 152 acts as an insulator between the plasma power supply 74 and the conductive portion 146 and the bar housing 148. The extrusion 152 may also releasably secure the plasma power supply 74 to the conductive portion 146, wherein a pair of downwardly angled ribs 154 keep the ion sources 78 properly aligned.

The plasma power supply 74 may include a high voltage power supply wire 156 that spans the length of the ionization assembly 72. The high voltage power supply wire 156 may carry electricity having a voltage ranging between about 2,000 Volts to about 8,000 Volts, including all points in-between. The high voltage power supply wire 156 creates an electric field and the conductive portion 146, which acts as a resistor, draws the electrons from the electric field. The electrons migrate through the conductive portion 146 and progress to the ion sources 77. The electricity output by the plasma power supply 74 may have an alternating current (AC) or direct current (DC) component, including a high frequency component that allows for adjustment of the ion concentration (e.g. a pulse wave). The conductive portion 146 and the ion sources 77 are designed to create positive ions, negative ions, or both simultaneously. The conductive portion 146 and ion sources 77 are designed to create a differential voltage for attraction or opposition of a flowing median of products within the flowing median, such as contaminants in air.

The ionization assembly 72 may be configured without the conductive portion 146. In accordance with this configuration, the ion sources 77 are positioned adjacent the plasma power supply 74 by the extrusion 152. The individual ion sources 77 are thus inserted into corresponding holes (not shown) within the bottom portion of the extrusion 152 and positioned adjacent the plasma power supply 74. Referring to FIGS. 2 and 5, it should be appreciated that the ionization assembly 72 itself may be disposed within the air channel 62 of the hand dryer assembly 20 or may simply include ion sources 78 that extend through the plenum 60 and into the air channel 62 with all other components of the ionization assembly 72 being disposed outside the air channel 62.

Figure 9:
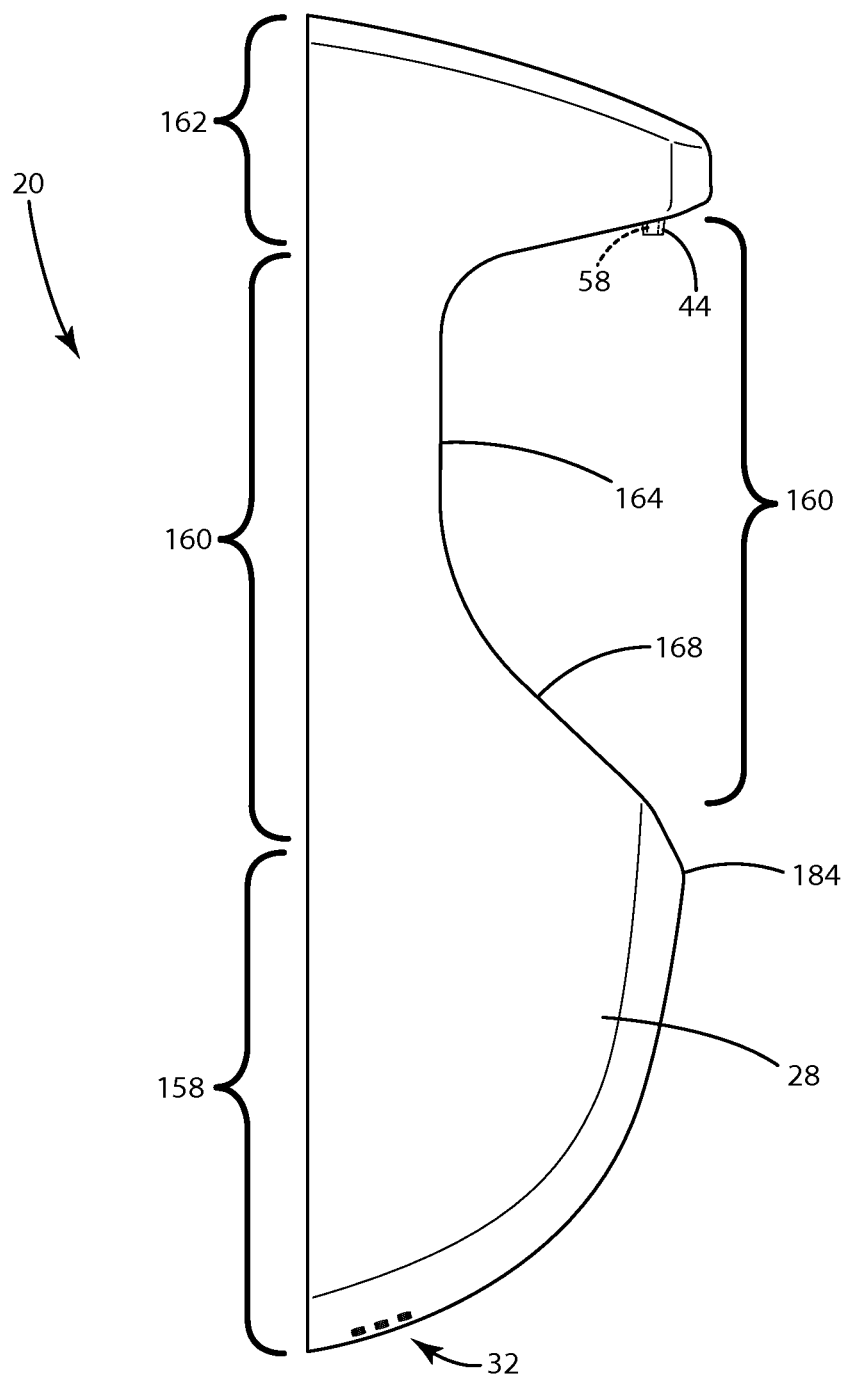
FIG. 9 is a side elevational view of the hand dryer assembly shown in FIG. 4.
Figure 10:
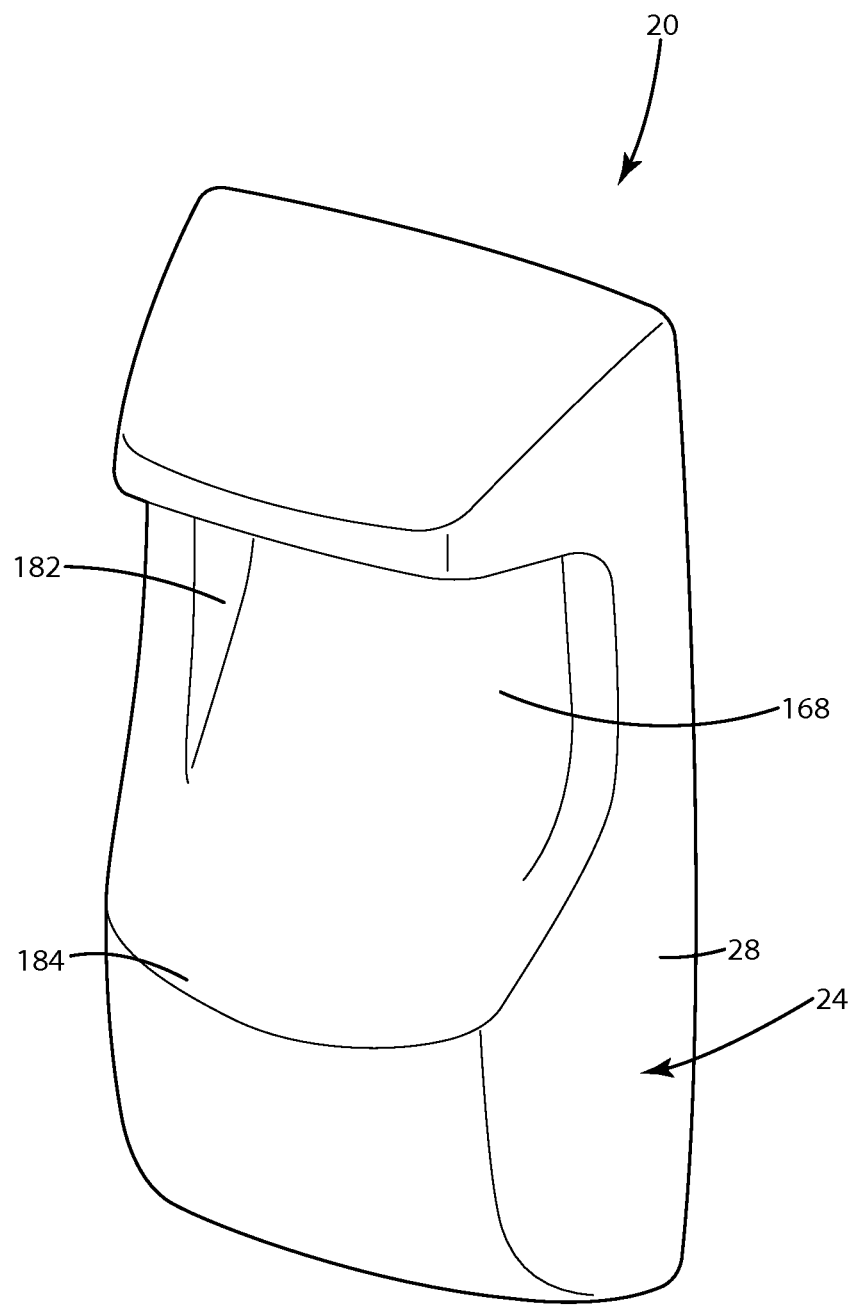
FIG. 10 is a front perspective view of the hand dryer assembly shown in FIG. 4.
Figure 11:
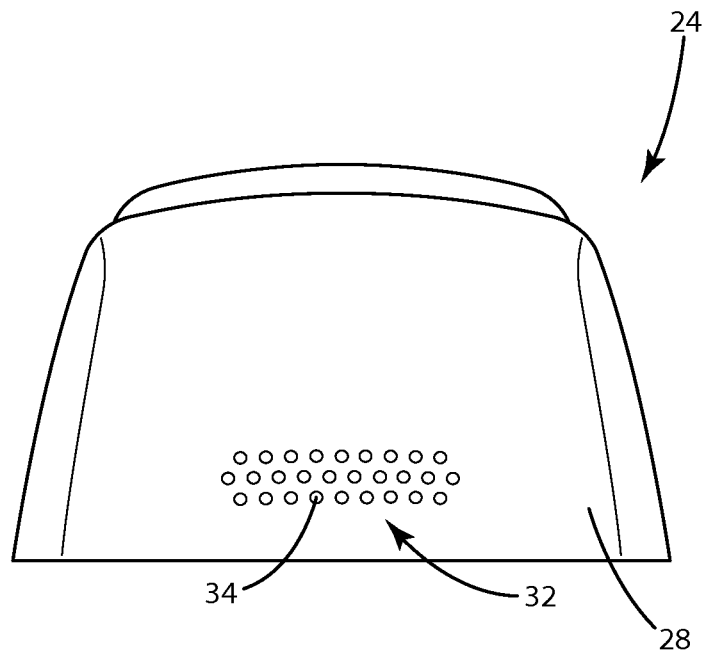
FIG. 11 is a bottom elevational view of the hand dryer assembly shown in FIG. 4.
Figure 12:
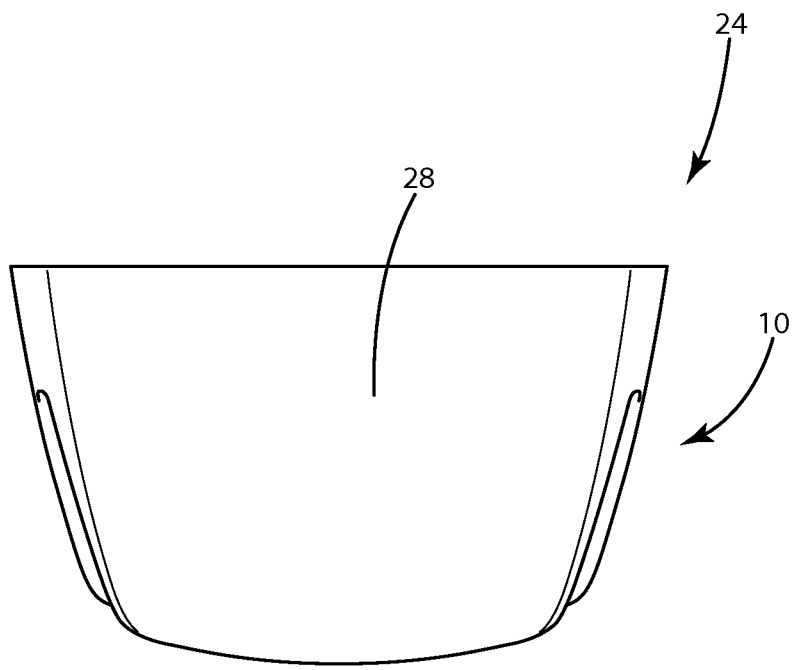
FIG. 12 is a top elevational view of the hand dryer assembly shown in FIG. 4.
Figure 13:
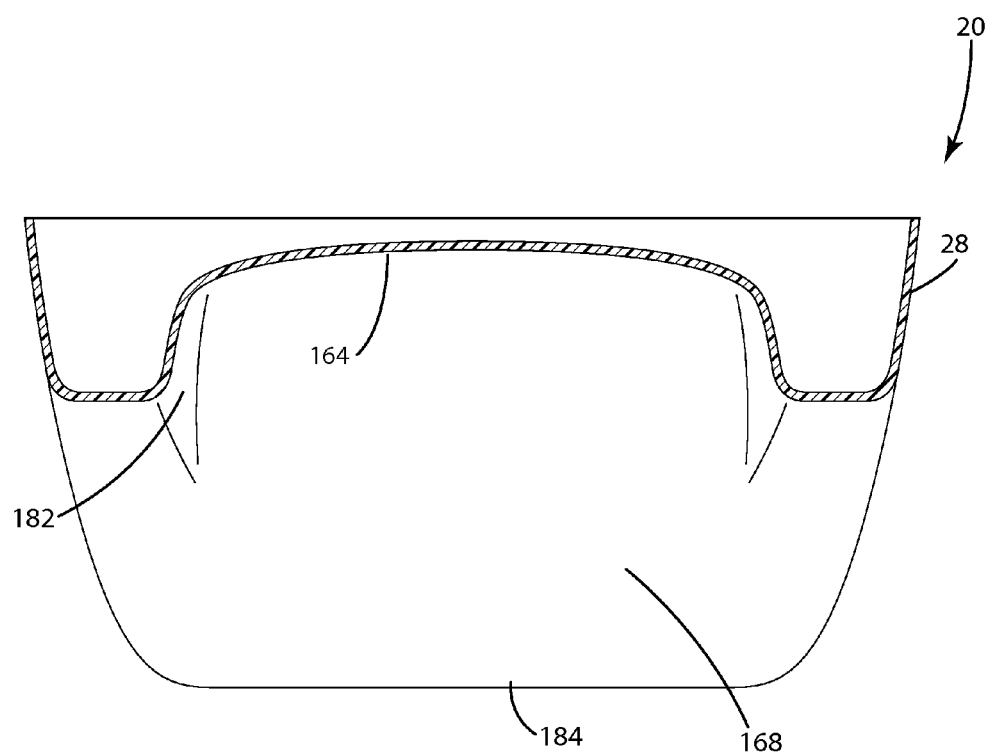
FIG. 13 is a top cross-sectional view of the outer shell of the hand dryer assembly shown in FIG. 4 taken along lines 13-13 and further illustrates the shape of the outer shell.

As shown in FIGS. 1 and 9, the hand dryer assembly 20 generally can be divided into a lower portion 158, a middle portion 160, and an upper portion 162, with reference to the outer shell 28. As illustrated in FIG. 1, the nozzle 58 and the air outlet 44 may be disposed adjacent the lower portion 158 of the outer shell 28. Accordingly, the blower assembly 36 may be disposed within the middle and upper portions 160, 162 of the outer shell 28 in this configuration. The air inlet 32 may take the form of a plurality intake vents 34 disposed in the lower portion 158 of the outer shell 28 and the plenum 60 may take the form of a duct connected to the blower housing 48 and the nozzle 58.

Now referring to FIG. 9, the hand dryer assembly 20 may alternatively be configured with the nozzle 58 and the air outlet 44 disposed adjacent the upper portion 162 of the outer shell 28. Accordingly, the blower assembly 36 may be disposed within the lower portion 158 of the outer shell 28 in this configuration and the air inlet 32 may take the form of a plurality intake vents 34 disposed in the lower portion 158 of the outer shell 28. The middle portion 160 of the outer shell 28 may thus present a contoured outer surface 164 being inwardly contoured to create an area for receiving the hands of the user. In other words, the contoured outer surface 164 may include a concave well or pocket in the middle portion 160 of the outer shell 28 for receiving the hands of the user. Now referring to FIGS. 14 and 21, the nozzle 58 and the air outlet 44 are located along the contoured outer surface 164 adjacent the upper portion 162 of the outer shell 28. The plenum 60 in this configuration may be integrally formed in the backplate 26. To accommodate the contoured outer surface 164 of the middle portion 160 of the outer shell 28, the plenum 60 integrally formed in the backplate 26 may include an air outlet chamber 166 extending horizontally from the backplate 26. It should be appreciated that the air outlet chamber 166 is disposed within the upper portion 162 of the outer shell 28 and communicates the moving air stream 38 to the nozzle 58. The ion sources 77 are then mounted at least partially within the air outlet chamber 166 of the plenum 60 such that the ion sources 77 are proximally located to the air outlet 44.

In the exemplary hand dryer assembly 20 illustrated in FIGS. 4-14 and 21-28, the user would place their hands under the air outlet 44 proximate to an evaporation surface 168, which forms an indentation on the contoured outer surface 164. It should be recognized that the outer shell 28 may be formed in a variety of sizes, shapes, styles, and configurations, however, the hand dryer assembly 20 illustrated in FIGS. 4-14 is generally configured to have the blower assembly 36 located on the opposing side of the air outlet 44 relative to the area where the user would place their hands for drying, such as the illustrated evaporation surface 168. This contrasts the hand dryer assembly 20 shown in FIGS. 1-2 which has a blower assembly 36 configured such that the air outlet 44 is directly proximate and in line with the blower assembly 36 such that the entire hand dryer assembly 20 is located on one side of the hands such as above or below the hands. The hand dryer assembly 20 shown in FIGS. 4-14, through locating the blower assembly 36 and the air outlet 44 on opposing sides of the operator's hands, allows for a uniquely shaped, efficient, low-profile, and ADA compliant hand dryer assembly 20 for location in high traffic areas. The configuration of the outer shell 28, the blower assembly 36, the backplate 26, and the air outlet 44 is more specifically illustrated in FIG. 21-28.

Figure 21:
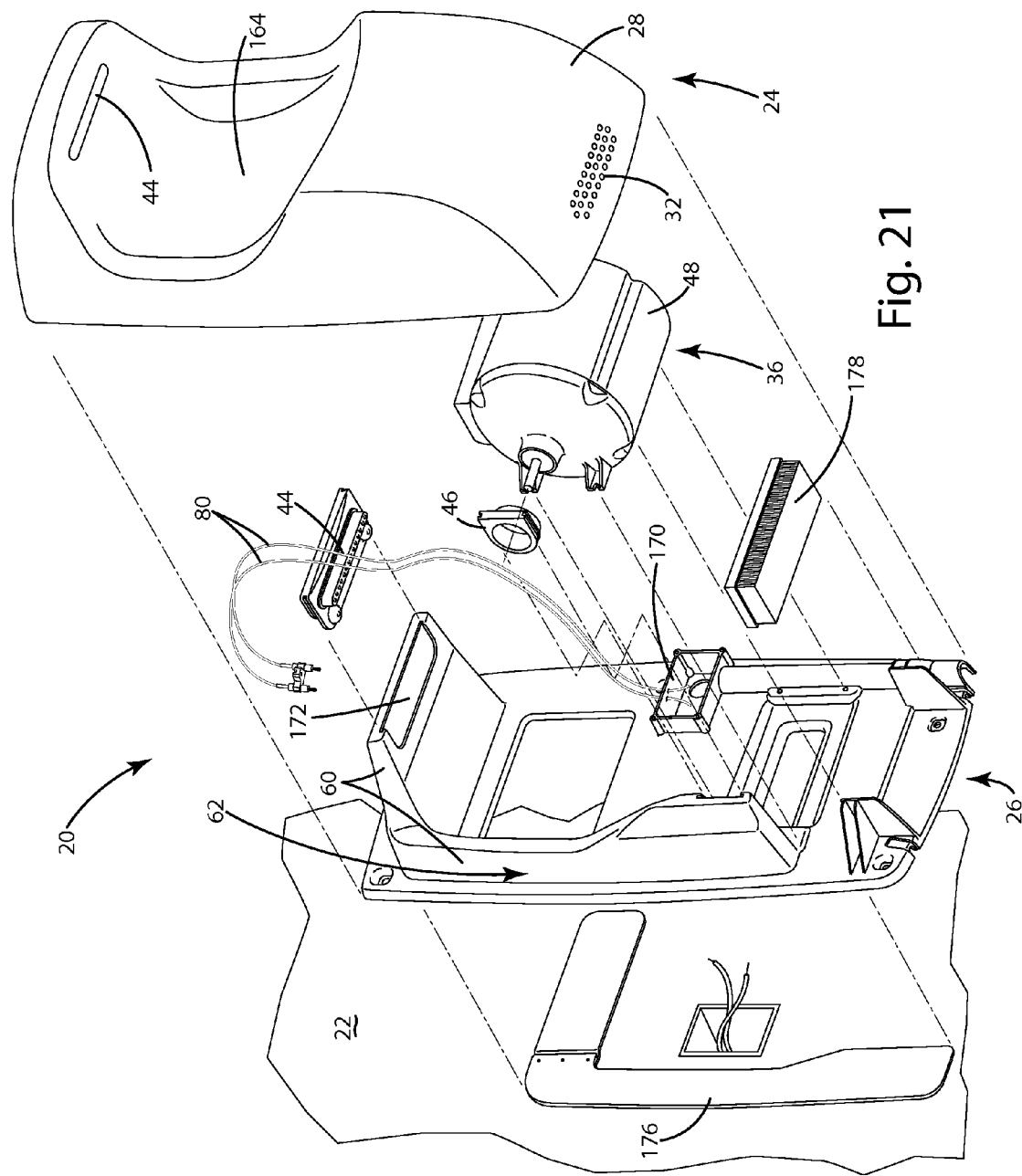
FIG. 21 is an exploded perspective view of the front of the hand dryer assembly shown in FIG. 4 and further illustrates the blower assembly and related component located within the housing.
Figure 22:
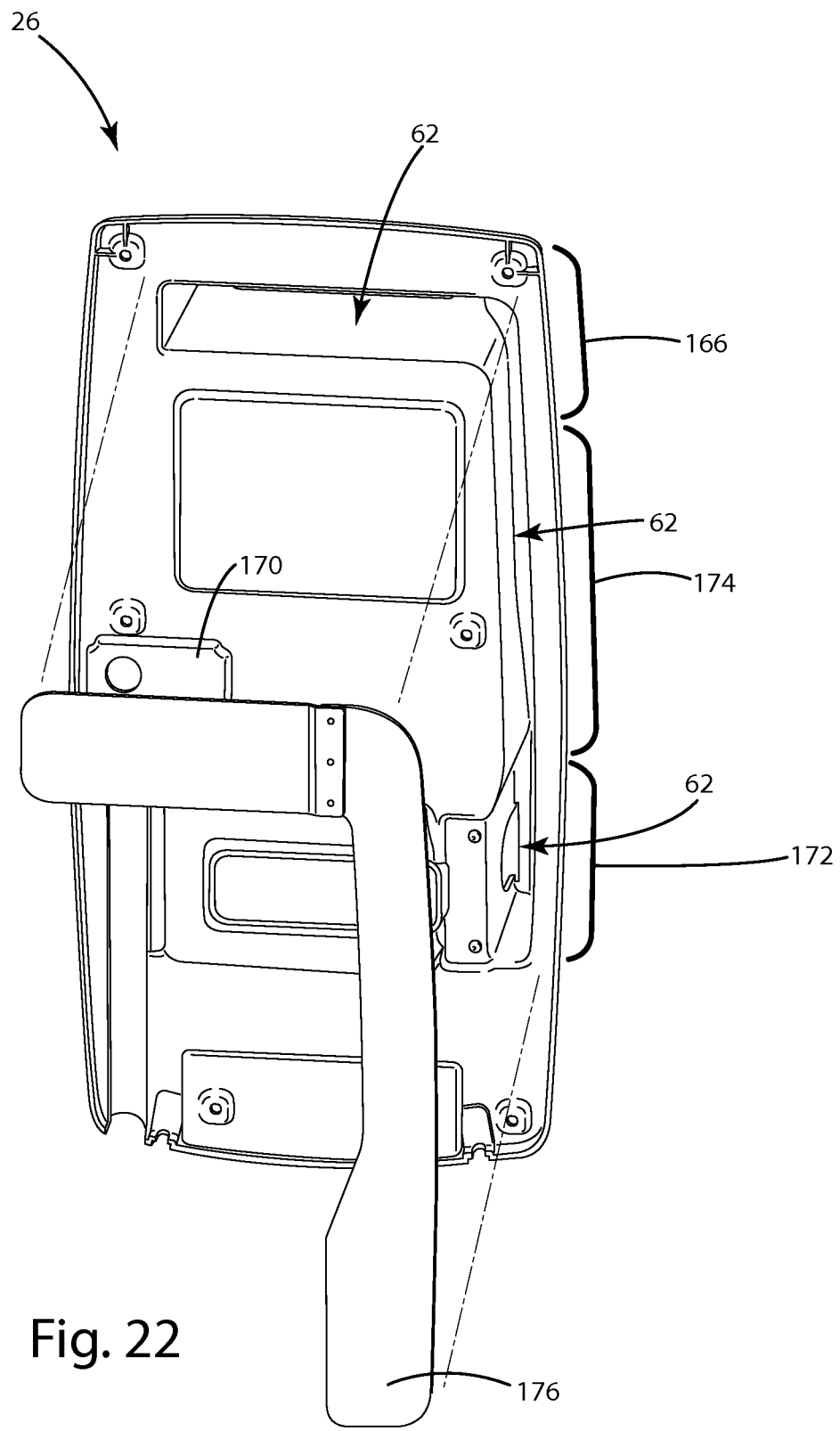
FIG. 22 is an exploded perspective view of the rear of the hand dryer assembly shown in FIG. 4 and further illustrates the backplate and the air channel integrally formed in the backplate.
Figure 23:
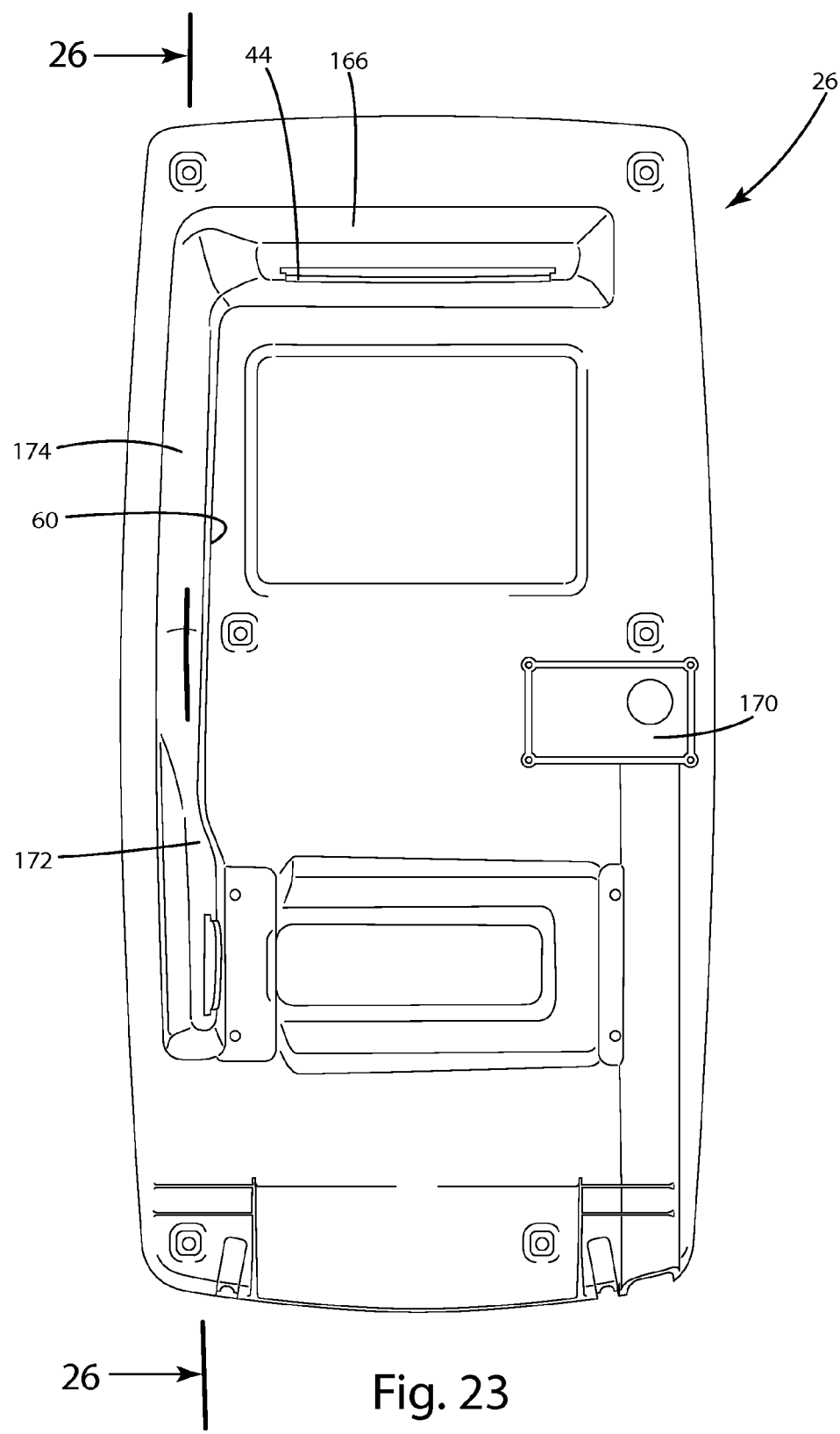
FIG. 23 is a rear elevational view of the backplate shown in FIG. 22.
Figure 24:
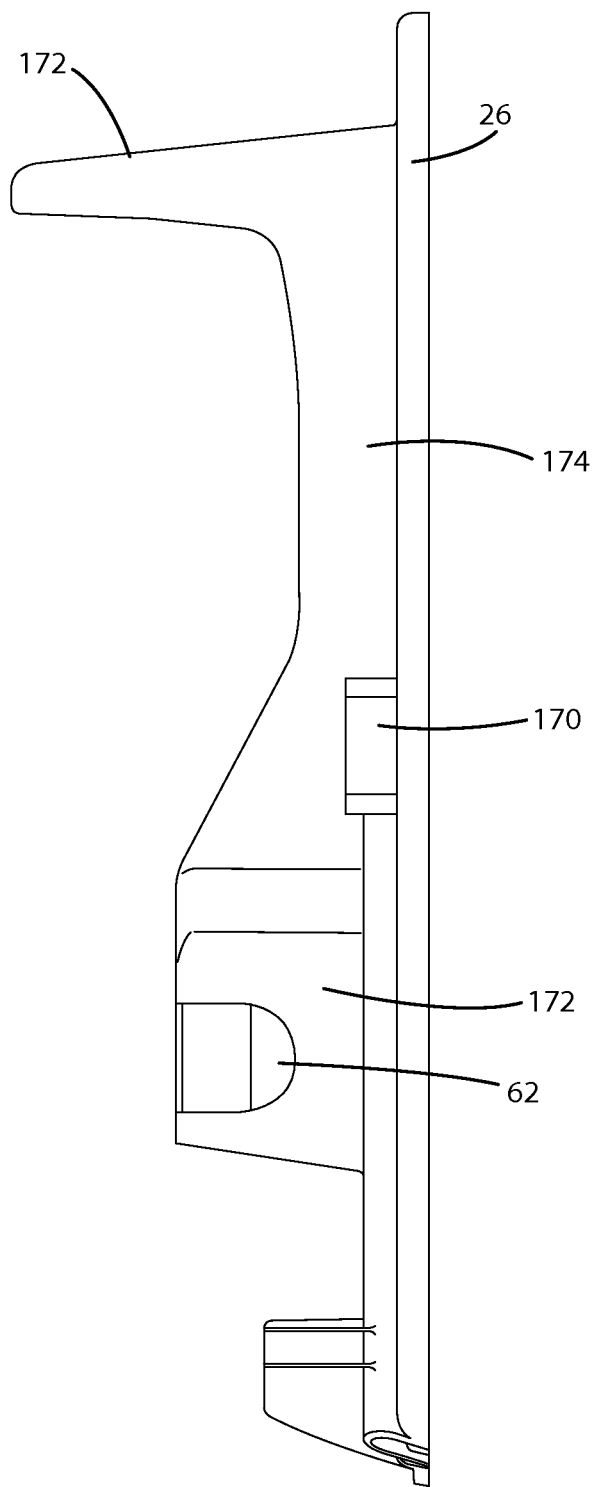
FIG. 24 is a right elevational view of the backplate shown in FIG. 22.
Figure 25:
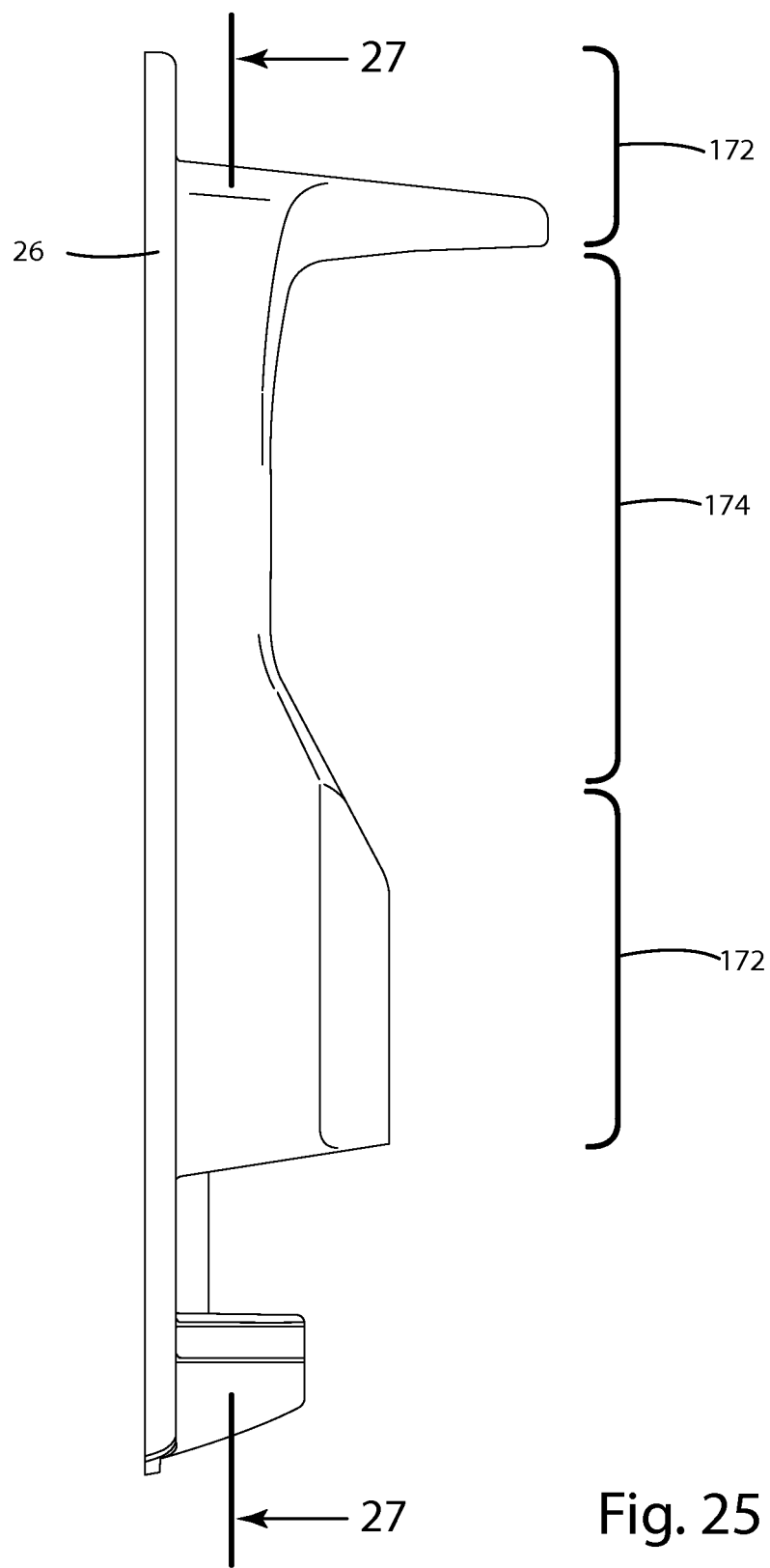
FIG. 25 is a left elevational view of the backplate shown in FIG. 22.
Figure 26:
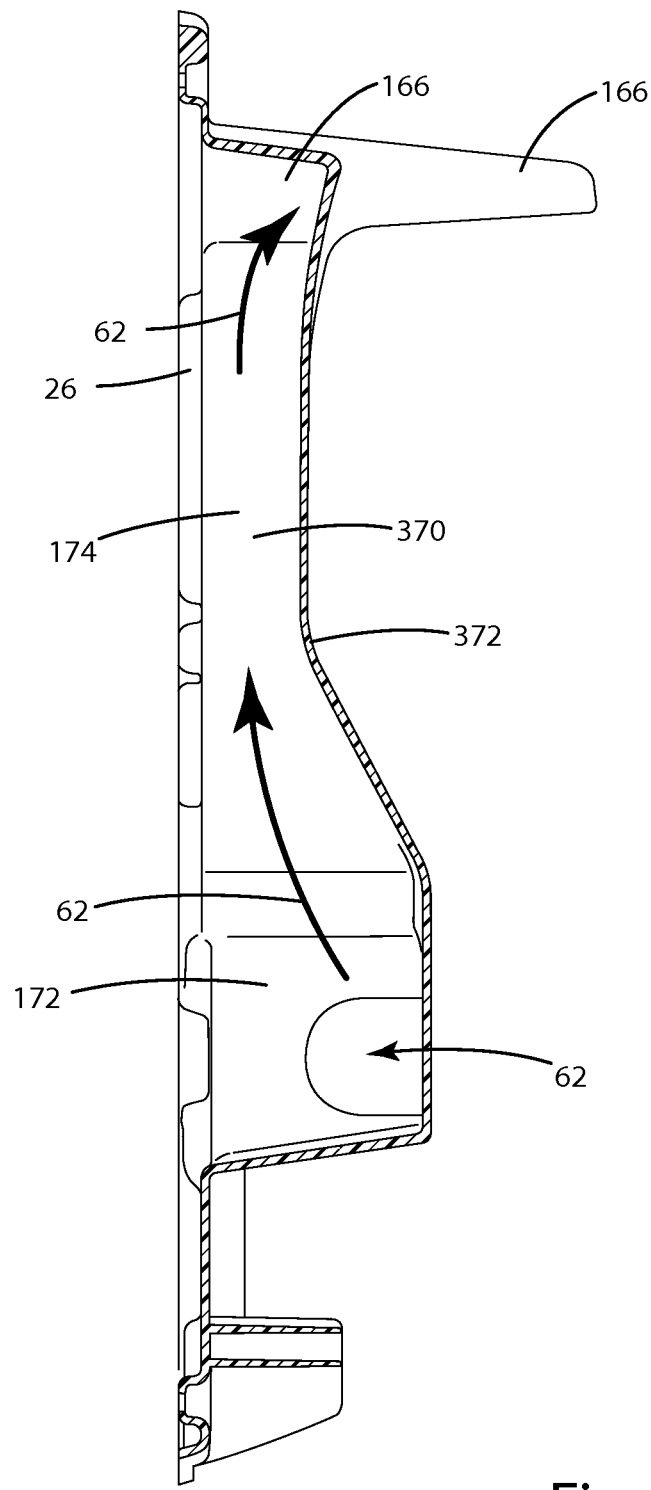
FIG. 26 is a partial cross-sectional view of the backplate shown in FIG. 22 taken along lines 26-26.
Figure 27:
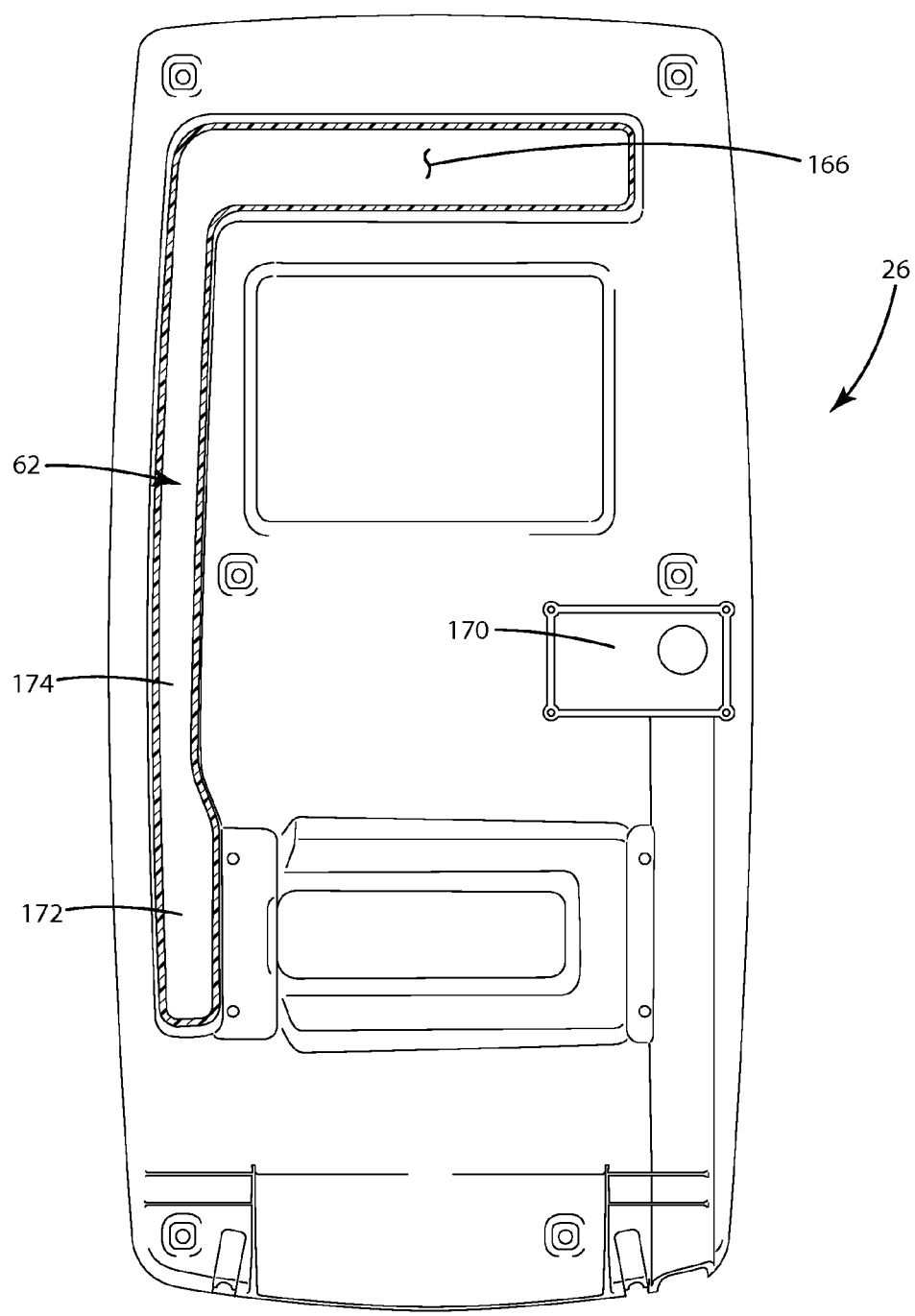
FIG. 27 is a partial cross-sectional view of the backplate shown in FIG. 22 taken along lines 27-27.

More particularly, the upper portion 162 of the outer shell 28 generally includes an air outlet 44 extending outward from the support surface 22. The adjacent middle portion 160 of the outer shell 28 is located on the contoured outer surface 164, where the outer shell 28 contours inward, creating an area for the user to place their hands under the air outlet 44. The lower portion 158 of the outer shell 28 generally includes an outward bulge from the support surface 22, to allow sufficient room for the blower assembly 36 in the outward bulge, as illustrated in FIG. 21.

Referring to FIGS. 22-28, the unique backplate 26 of the hand dryer assembly 20 provides a contoured one piece member to channel air from a blower assembly 36 to air outlet 44 with minimal assembly and is a space-saving configuration. More specifically, it is very difficult to provide a hand dryer assembly 20 where the blower assembly 36 is located on the opposite side of the air outlet 44 of where the user places their hands for drying, without using expensive, hard to assemble tubing, while maintaining sufficient air flow between the blower assembly 36 and the air outlet 44. Since the high-speed air passing through the tubing exhibits fluid characteristics, the tubing itself creates design limitations on how much and how fast the air can flow through, while also minimizing the power requirements of the blower assembly 36. For a hand dryer assembly 20, as illustrated in FIG. 21, having an outer contoured surface 164 as illustrated, it is almost impossible to channel air from the blower assembly 36 to the air outlet 44 with the use of tubing, as the outer shell 28 would substantially minimize the cross sectional area of any such tubing. More specifically, it would not only be difficult to assemble given the minimal space, particularly in the middle portion 160 of the outer shell 28, but any type of tubing or separate channels routing the air would be susceptible to reduced air output, particularly with high-speed hand dryers.

The backplate 26 disclosed includes an integrally formed plenum 60 and allows for easy assembly and improved fluid transfer of the air between the blower assembly 36 and air outlet 44. In addition, the backplate 26 is specifically configured to allow for easy replacement of existing dryers by having areas that sit proud of the support structure 22, when the hand dryer assembly 20 is mounted on the support structure 22, thereby allowing easy routing of power from an electrical service disposed along the wall to an integral electrical box 170 on the backplate 26. The integrally formed plenum 60 defines the air channel 62 that is specifically configured to induce velocity changes in the fluid movement of the air through the air channel 62 and thereby reduce the noise emitted by the hand dryer assembly 20 during operation. The air channel 62 may be divided into three distinct areas, specifically an air entrance chamber 172, an air passageway 174, and the air outlet chamber 166, each having different volumes and cross sectional areas to provide improved air flow and reduced noise. One current issue with high-speed hand dryers is that the noise, particularly when multiple dryers operate in a washroom having hard surfaces, the combined noise can be extremely loud. The configuration of the backplate 26 and specifically the air channel 62 defined by the backplate 26 all work together to reduce noise.

The backplate 26 is expected to be formed out of a composite material. For example, the backplate 26 may be injection molded with all of the illustrated features directly formed on the backplate 26 for easy assembly. The backplate 26 may be formed out of a semi-crystalline polybutylene terephthalate material, which provides the desired structural rigidity, is heat resistive, and includes sound absorbing properties. More specifically, the backplate 26 is preferably formed out of a heat resistive material having acoustic impedance. Of course, the backplate 26 may be formed from other materials, such as Acrylonitrile butadiene styrene or polycarbonate.

The air outlet chamber 166 is specifically configured to have a decrease in velocity of the air relative to the other portions of the air channel 62, such as through having an increased volume relative to the air passageway 174 and air entrance chamber 172. More specifically, the air outlet chamber 166 is configured to allow for a velocity of air reduction due to the expanded space relative to the air passageway 174. This drop in velocity of the air reduces the noise and as such, provides a quiet hand dryer assembly 20. Of course, the air outlet chamber 166 may be formed in a variety of sizes, styles and configurations, which partially depend on the shape of the upper portion 162 of the outer shell 28. Additionally, the backplate 26 may be molded with the air channel 62 in place and an air passage cover plate 176 installed over the air channel 62. Although not illustrated, a gasket seal may also be used to seal the air channel 62 and prevent any air from exiting the air channel 62, other than through the air outlet 44.

During operation, a user would place their hands near the middle portion 160 of the outer shell 28 at which time the motion sensor 70 would instruct the blower assembly 36 to initiate its cycle. Power would be supplied from the electrical box 170 to the blower assembly 36 which supplies the moving air stream 38 to the air channel 62. It should be appreciated that the blower assembly 36 generates the moving air stream 38 by drawing ambient air 30 in through the air inlet 32 in the outer shell 28 and if desired, through the optional filter 178. The blower assembly 36 is expected to be a high-speed unit producing an air speed or velocity of at least 10,000 LFM at the air outlet 44 and would force air into the air entrance chamber 172. The moving air stream 38 may be specifically directed against the walls creating a turbulent effect and then is squeezed down through the air passageway 178 increasing the velocity of the moving air stream 38. As the moving air stream 38 enters the air outlet chamber 166, it expands, reducing the velocity of the moving air stream 38, which reduces the noise level associated with operation of the blower assembly 36 and the moving air stream 38 being forced through the air channel 62. The moving air stream 38 then exits through the nozzle 58 and specifically through the air outlet 44. After a certain amount of time when no hands are detected by the motion sensor 70, the blower assembly 36 would cycle down.

The hand dryer assembly 20 disclosed may further include a splash guard 180 either integrated into the contoured outer surface 164 of the outer shell 28 or separately disposed on an existing wall or support structure 22. The hand dryer assembly 20 having the integrated splash guard 180 is generally illustrated in FIGS. 4-14 and 21-28, while FIGS. 15-20 show a separate splash guard 180 is mounted below the hand dryer assembly 20. Each of these hand dryer assemblies 20 include a splash guard 180 generally includes the evaporation surface 168, as well as sidewalls 182 that cooperate to prevent moisture and water from being blown off a person's hands to surrounding support structure 22 such as walls and floor. In addition, the evaporation surface 168 and sidewalls 182 cooperate and are so configured that moisture being blown off of the hands onto the splash guard 180, especially during high-speed hand drying, is substantially changed from the liquid to the gaseous state while on the evaporation surface 168. As such, even when moisture is blown off the hands onto the evaporation surface 168, it accumulates and runs down the evaporation surface 168 from the moving air stream 38 velocity pushing it down the evaporation surface 168. The evaporation surface 168 is specifically configured to ensure that the moisture evaporates before it is ejected off an outer lip 184 of the evaporation surface 168 at the end of the evaporation surface 168. More specifically, as the splash guard 180, specifically the evaporation surface 168 and sidewalls 182 trap and accumulate moisture. The profile of the evaporation surface 168 is configured to evaporate any moisture before it is ejected onto a user's clothing or the floor. Thus, the splash guard 180 is substantially beneficial to facilities when properly mounted for functional use, as the hand dryer assembly 20 and the splash guard 180 will have a portion below the 27" from floor height, allowing the hand dryer assembly 20 with integral splash guard 180, as well as the hand dryer assembly 20 with the separate splash guard 180, to be mounted in hallways and protrude more than four inches from the wall, and yet be in compliance with ADA requirements. In summary, the splash guard 180 addresses problems associated with water or moisture being ejected off of the user's hands to surrounding surfaces, as well as providing an ADA compliant package.

Figure 34:
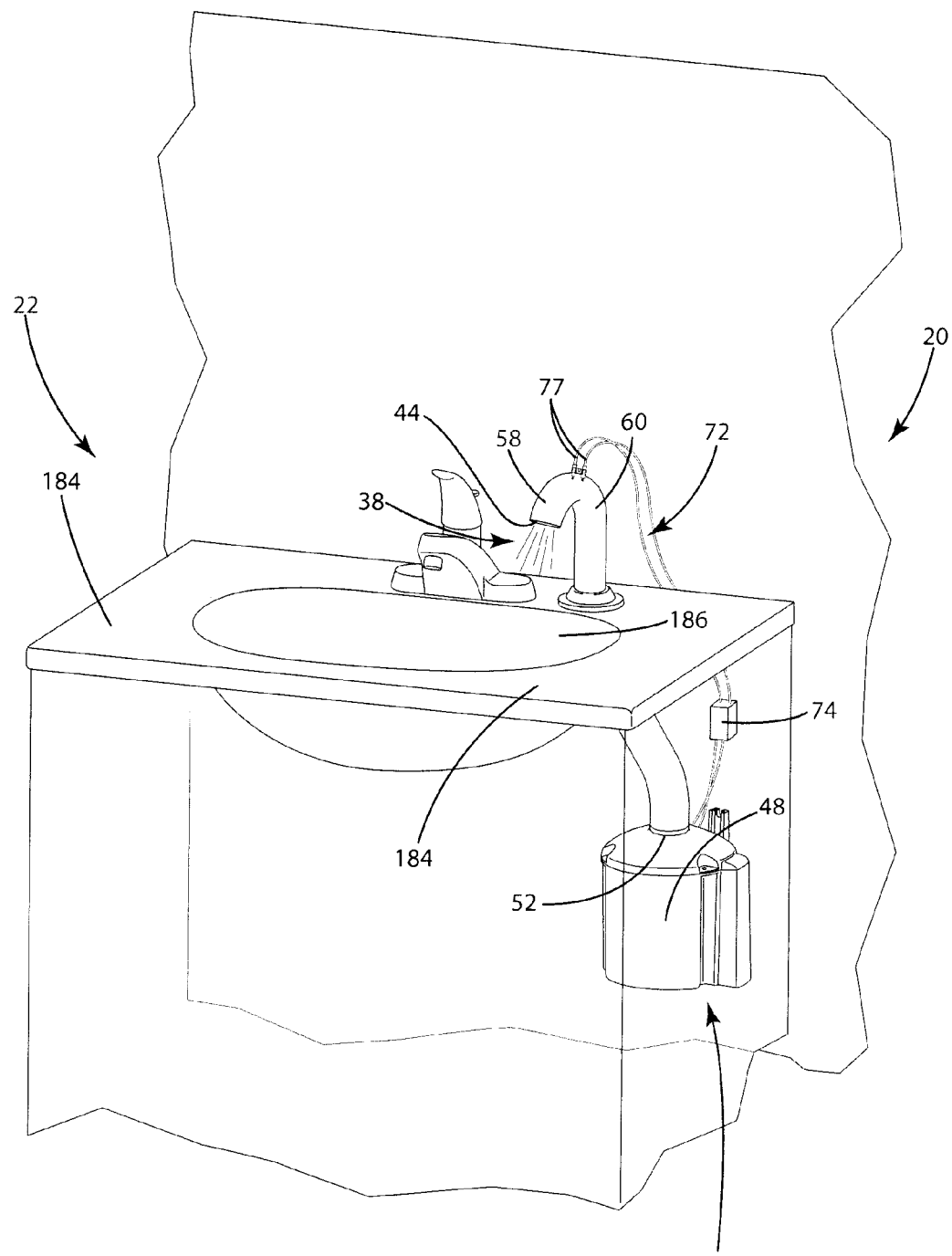
FIG. 34 is a front perspective view of an exemplary hand dryer assembly of the subject invention where the hand dryer assembly is installed in a countertop adjacent a sink.

Referring to FIG. 34, the hand dryer assembly 20 disclosed may be installed in support structure 22 comprising a countertop 184, and more particularly a countertop 184 adjacent a sink 186. In this configuration, the hand dryer assembly 20 may not have the outer shell illustrated in the other Figures. Instead, the blower assembly 36 may generally be mounted beneath the countertop 184. As with the other configurations, the blower assembly 36 may have a blower housing 48 presenting an outlet window 52. The plenum 60 may generally extend from the outlet window 52 to a nozzle 58 disposed above the countertop 184. Accordingly, the plenum 60 may generally extend through the countertop 184 and communicates the moving air stream 38 from the blower assembly 36 to the air outlet 44 defined by the nozzle 58. As such, the moving air stream 38 may generally be directed into the sink 186 by the nozzle 58. This is advantageous because water from the user's hands is simply blown off the hands and back into the sink 186. As in the other configurations, the hand dryer assembly 20 may include an ionization assembly 72. Again, the ion sources 77 of the ionization assembly 72 are generally positioned in the plenum 60, preferably adjacent the nozzle 58. The plasma power supply 74 of the ionization assembly 72 is electrically connected to the ion sources 77 and may be installed below the countertop 184 along with the blower assembly 36. As such, the charged ions generated by the ion sources 77 may advantageously sanitize surfaces of the sink 186 and areas of the adjacent countertop 184.

Referring again to FIG. 3, an ionization assembly 72 for producing charged ions from an electrical voltage difference is disclosed. Such an ionization assembly 72 may advantageously be used in hand dryer assemblies 20 or in other applications to sanitize the air or other objects. Such an ionization assembly 72 generally includes a power supply 74 generating electricity having a high voltage difference and at least one pair of carbon brushes 78 electrically connected to the power supply 74. Accordingly, the carbon brushes 78 receive electricity from the power supply 74 such that the carbon brushes 78 have opposing charges at any given time. It should be appreciated that opposing charges, as used herein, is meant to describe a voltage difference between the carbon brushes 78 such that one of the carbon brushes 78 is positively charged while the other carbon brush 78 is negatively charge at a given moment in time. It should also be appreciated that direct current (DC) or alternating current (AC) electricity can be used and that where alternating current (AC) electricity is used the charges of the carbon brushes 78 may vary with time but always oppose each other. Additionally, the power supply 74 may step-up the voltage of the electricity. In other words, the power supply 74 may receive electricity of a pre-determined voltage and generate electricity having a voltage that is greater than the pre-determined voltage for transmission to the carbon brushes 78.

The ionization device 72 includes a brush holder 92 supporting the carbon brushes 78 in an aligned and spaced relationship with respect to one another. Again, the term aligned describes an arrangement of the carbon brushes 78 where the central axes A of the carbon brushes 78 generally extend in the same direction such that any angle between the central axes A is small. Preferably, the central axes A of the carbon brushes 78 are parallel and spaced apart from one another. A plurality of bristles 90 extend from each of the carbon brushes 78 with each bristle 90 including a bristle base 88 and a bristle end 86. The bristle base 88 receives electrons from the electricity supplied by the power supply 74 and the bristle end 86 discharges the electrons as charged ions in response to the electrons flowing from the bristle base 88 to the bristle end 86. The pair of carbon brushes 78 are electrically connected to the power supply 74 by a pair of high voltage leads 80. More particularly, the bristles 90 of the carbon brushes 78 are attached to the pair of high voltage leads 80 by an electrical crimp connector that receives the bristle bases 88.

Preferably, carbon brushes 78 are spaced apart with a center-to-center distance b ranging between 18 millimeters and 23 millimeters. Additionally, each of said bristles 90 may be configured to have an exposed length ranging between 2 millimeters (mm) and 4 millimeters (mm) and the bristle base 88 may have a diameter ranging between 0.0762 millimeters (mm) and 0.381 millimeters (mm). It should be appreciated that the term exposed length, as used herein, is measured along the portion of the bristle 90 that is exposed to the air. For each carbon brush 78, the plurality of bristles 90 are arranged together form a clump. This clump may be configured to have an overall diameter ranging between 2 millimeters (mm) and 4 millimeters (mm) as measured circumferentially around the clump adjacent the bristle ends 86 and an overall diameter ranging between 1 millimeter (mm) and 2 millimeters (mm) as measured circumferentially around the clump adjacent the bristle bases 88.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. A hand dryer assembly for drying the hands of a user, said hand dryer assembly comprising:
    a blower assembly for generating a moving air stream having an operational cycle with a normal airstream velocity of at least 10,000 linear feet per minute,
    an air channel extending from an air inlet through said blower assembly to an air outlet;
    an ionization assembly including a plasma power supply electrically coupled to at least two ion sources and wherein said at least two ion sources are at least partially disposed within said air channel, and wherein said ionization assembly is at least partially disposed within an outer shell and free from glass and wherein said ionization assembly is configured to avoid the production of ozone; and
    a motion sensor capable of detecting a user activation through the presence of the hands of the user and configured to activate said blower assembly and said ionization assembly in response to the user activation, and wherein the blower assembly and ionization assembly after removal of the user activation are configured to operate for at least a specified time interval at a reduced air stream velocity.

2. A hand dryer assembly of claim 1 wherein each of said ion sources include a base and a plurality of carbon fibers extending from said base.

3. A hand dryer assembly of claim 2 wherein each of said bases are electrically coupled to said plasma power supply and have opposing and alternating charges during operation.

4. A hand dryer assembly of claim 1 wherein said ion sources are located proximate to said air outlet.

5. A hand dryer assembly of claim 1 further including a power source supplying electricity of a pre-determined voltage to said blower assembly and wherein said plasma power supply is electrically connected to said power source to receive electricity therefrom and generate electricity having a voltage that is greater than the pre-determined voltage.

6. A hand dryer assembly of claim 1 wherein said ion sources are located transversely to said air channel.

7. A hand dryer assembly of claim 6 wherein said ionization assembly includes a brush holder supporting said ion sources in parallel and spaced relationship with respect to one another.

8. A hand dryer assembly of claim 1 wherein said ion sources are at least one pair of carbon brushes disposed in spaced apart arrangement with a center-to-center distance ranging between 18 millimeters and 23 millimeters.

9. A hand dryer assembly of claim 1 wherein said ion sources are at least one pair of carbon brushes each presenting a plurality of bristles with each bristle including a base and a pointed end for stripping electrons from electricity generated by said plasma power supply as the electrons flow from said base to said pointed end where the electrons are discharged into the moving air stream as charged ions.

10. A hand dryer assembly of claim 1 further including a controller electrically connected to said blower assembly for supplying alternating current electricity of a pre-determined voltage to said blower assembly and wherein said ionization assembly includes at least one pair of carbon brushes being oppositely charged and electrically connected to said plasma power supply to receive electricity from said plasma power supply and emit charged ions of opposite charges into the moving air stream.

11. A hand dryer assembly of claim 1 wherein said ion sources are a pair of carbon brushes mounted perpendicularly along said air channel such that said pair of carbon brushes extend transversely to a flow direction of the moving air stream.

12. A hand dryer assembly of claim 1 wherein said plasma power supply of said ionization assembly receives electricity from said hand dryer assembly through a pair of power leads and supplies electricity to said ion sources through a pair of high voltage leads.

13. A hand dryer assembly of claim 1 wherein said air outlet is spaced from and disposed vertically above said blower assembly and said air channel includes an air expansion chamber extending above said blower assembly to said air outlet and said ion sources of said ionization assembly being mounted to said air expansion chamber.

14. A hand dryer assembly of claim 1 wherein said air outlet is disposed vertically below said blower assembly and said air channel includes a plenum extending between said blower assembly and said air outlet and said ion sources of said ionization assembly being mounted to said plenum.

15. A hand dryer assembly of claim 1 wherein said ion sources are at least a pair of carbon brushes extending through a wall forming said air channel.

16. A hand dryer assembly of claim 1 wherein said ion sources are disposed along a holder extending transversely within said air channel.

17. A hand dryer assembly of claim 1 further comprising a housing including a backplate and an outer shell defining at least one of said air inlet and said air outlet.

18. A hand dryer assembly of claim 1 further including a heating element mounted within said air channel and said heating element increasing the temperature of said moving airstream exiting said air outlet to between 55 and 75 degrees Fahrenheit above ambient room temperature.

19. A hand dryer assembly of claim 1 wherein said blower assembly and said ion sources are programmed to operate for at least a specified time interval at a reduced air stream velocity after each normal operational cycle.

20. A hand dryer assembly of claim 19 wherein said reduced airstream velocity is less than 3,000 linear feet per minute and has a volume flow rate of less than 25 cubic feet per minute and wherein said operational cycle has a normal air stream velocity of at least 10,000 linear feet per minute.

21. A hand dryer assembly for drying the hands of a user comprising:
    an outer shell,
    a blower assembly disposed within said outer shell for generating a moving air stream having a velocity of at least 10,000 LFM and a volume flow rate of less than 100 CFM,
    an air outlet for discharging the moving air stream from said hand dryer assembly into ambient air disposed outside said outer shell,
    an air channel extending through said blower assembly and to said air outlet for communicating the moving air stream to said air outlet, and
    an ionization assembly including a plasma power supply and at least two ion sources disposed at least partially within said air channel emitting charged ions directly into the moving air stream to sanitize the hands of the user and the moving air steam and the ambient air entrained into the moving air stream after the moving air stream exits said air outlet and wherein said ionization assembly is configured to avoid the production of ozone and wherein said at least two ion sources are free from glass, and wherein said at least two ion sources alternate between positive and negative and at least one of said two ion sources is proximate to a grounded biasing element; and
    a motion sensor for sensing activating the blower assembly and ion assembly in response to a user activation and wherein the blower assembly and ionization assembly after removal of the user activation are configured to operate for at least a specified time interval at a reduced air stream velocity of less than 3,000 linear feet per minute.

22. A hand dryer assembly of claim 21 wherein each of said ion sources include a base and a plurality of carbon fibers extending from said base.

23. A hand dryer assembly of claim 22 wherein each of said bases are electrically coupled to a plasma power supply and have opposing charges during operation.

24. A hand dryer assembly of claim 21 wherein said ion sources are located proximate to said air outlet.

25. A hand dryer assembly of claim 21 further including a power source supplying an electricity of a pre-determined voltage to said blower assembly and wherein said plasma power supply is electrically connected to said power source to receive electricity therefrom and generate electricity having a voltage that is greater than the pre-determined voltage.

26. A hand dryer assembly of claim 1 wherein said ion sources are located transversely to said air channel.

* * * * *